United States Patent
Kosuge et al.

(10) Patent No.: US 9,051,232 B2
(45) Date of Patent: Jun. 9, 2015

(54) PERYLENE COMPOUND AND ORGANIC LIGHT EMITTING DEVICE USING THE COMPOUND

(75) Inventors: Tetsuya Kosuge, Yokohama (JP); Satoshi Igawa, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 236 days.

(21) Appl. No.: 13/131,853
(22) PCT Filed: Nov. 27, 2009
(86) PCT No.: PCT/JP2009/070358
§ 371 (c)(1),
(2), (4) Date: May 27, 2011

(87) PCT Pub. No.: WO2010/064694
PCT Pub. Date: Jun. 10, 2010

(65) Prior Publication Data
US 2011/0227057 A1  Sep. 22, 2011

(30) Foreign Application Priority Data
Dec. 1, 2008  (JP) ................. 2008-305859

(51) Int. Cl.
| H01L 51/54 | (2006.01) |
| C07C 13/62 | (2006.01) |
| C07C 13/547 | (2006.01) |
| C07C 23/38 | (2006.01) |
| C07D 401/14 | (2006.01) |
| C07D 403/14 | (2006.01) |
| C07C 13/567 | (2006.01) |
| C07C 13/18 | (2006.01) |
| C07C 13/66 | (2006.01) |
| C07C 15/20 | (2006.01) |
| C07C 22/08 | (2006.01) |
| C07D 213/53 | (2006.01) |
| C07D 239/26 | (2006.01) |
| C09K 11/06 | (2006.01) |
| H01L 51/00 | (2006.01) |
| H05B 33/10 | (2006.01) |
| H05B 33/14 | (2006.01) |
| H01L 51/50 | (2006.01) |

(52) U.S. Cl.
CPC .............. *C07C 13/567* (2013.01); *C07C 13/18* (2013.01); *C07C 13/66* (2013.01); *C07C 15/20* (2013.01); ......... *C07C 22/08* (2013.01); *C07C 2101/14* (2013.01); *C07C 2103/18* (2013.01); *C07C 2103/26* (2013.01); *C07C 2103/40* (2013.01); *C07C 2103/48* (2013.01); *C07D 213/53* (2013.01); *C07D 239/26* (2013.01); *C09K 11/06* (2013.01); *C09K 2211/1011* (2013.01); *C09K 2211/1029* (2013.01); *C09K 2211/1044* (2013.01); *H01L 51/0058* (2013.01); *H01L 51/5012* (2013.01); *H01L 51/5048* (2013.01); *H05B 33/10* (2013.01); *H05B 33/14* (2013.01)

(58) Field of Classification Search
None
See application file for complete search history.

(56) References Cited

U.S. PATENT DOCUMENTS
| 2003/0219625 A1* | 11/2003 | Wolk et al. ............. 428/690 |
| 2005/0048313 A1 | 3/2005 | Sotoyama |
| 2005/0088082 A1* | 4/2005 | Morita et al. ........... 313/504 |

FOREIGN PATENT DOCUMENTS
| JP | H09-241629 A | 9/1997 | |
| JP | H10-036832 A | 2/1998 | |
| JP | 2001-196180 A | 7/2001 | |
| JP | 2003-104916 A | 4/2003 | |
| JP | 2005-041804 A | 2/2005 | |
| JP | 2005041804 A * | 2/2005 | ............. C07C 15/56 |
| JP | 2005-113072 A | 4/2005 | |
| JP | 2009-292807 A | 12/2009 | |
| WO | 03/090502 A2 | 10/2003 | |
| WO | 2005/040303 A1 | 5/2005 | |

OTHER PUBLICATIONS

Machine English translation of JP 2005-041804 A. Aug. 15, 2012.*
Dependence of Conductivity and Ferromagnetic Behavior of Pyrolyzed Aromatic Tetracarboxylic Acid Sodium Salts on Molecular Structure., Technol Rep Kansai Univ, 1997, No. 39, p. 235-244.
Database WPI Week 200535 Thomson Scientific, London, GB; AN 2005-336141 XP002729880, & JP 2005 068366 A (Toyo Ink Mfg Co Ltd) Mar. 17, 2005.

* cited by examiner

*Primary Examiner* — J. L. Yang
(74) *Attorney, Agent, or Firm* — Canon USA Inc. IP Division

(57) ABSTRACT

Provided is an organic light emitting device having high light emitting efficiency and good emission color purity. The organic light emitting device includes an anode, a cathode, and an organic compound layer which is sandwiched between the anode and the cathode, in which one of the anode and the cathode is transparent or semi-transparent and the organic compound layer contains at least one kind of perylene compound represented by the following general formula (1):

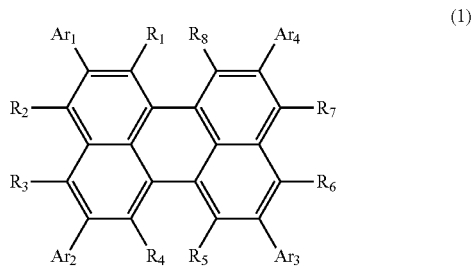

(1)

where $R_1$ to $R_8$ each represent a hydrogen atom or a substituted or unsubstituted alkyl group; and $Ar_1$ to $Ar_4$ each represent a substituent represented by the following general formula (2) or (3).

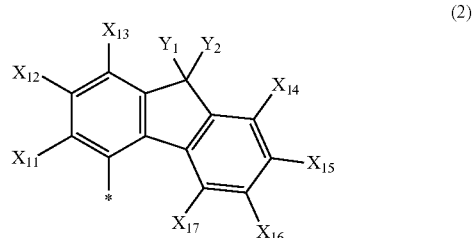

(2)

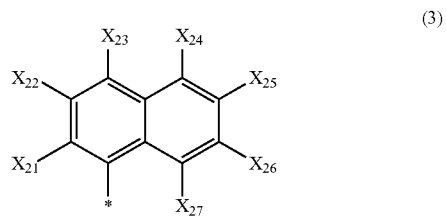

(3)

6 Claims, 2 Drawing Sheets

PERYLENE COMPOUND AND ORGANIC LIGHT EMITTING DEVICE USING THE COMPOUND

TECHNICAL FIELD

The present invention relates to a perylene compound and an organic light emitting device using the compound.

BACKGROUND ART

An organic light emitting device is an electronic device in which a thin film including a fluorescent light emitting organic compound or a phosphorescent light emitting organic compound is sandwiched between an anode and a cathode. Further, electrons and holes are injected from the respective electrodes to generate exciton of the fluorescent light emitting organic compound or the phosphorescent light emitting organic compound, whereby the organic light emitting device emits light when the exciton returns to a ground state.

Recent progress of an organic light emitting device is remarkable, and the progress of the device enable a light emitting device with a high luminance at a low applied voltage, a variety of emission wavelengths, high-speed responsiveness, and thin and light weight. From this fact, it is suggested that the organic light emitting device have potential to find use in a wide variety of applications.

However, the present situation calls for optical output with even higher luminance and higher light emitting efficiency. In addition, many problems still remain to be solved regarding durability against the change over time due to long-term use, deterioration caused by atmospheric gas containing oxygen, moisture, or the like. Further, when considering application to a full color display or the like, the present art is still insufficient against problems relating to the needs for light emission of blue, green, and red colors with high color purity.

In view of the foregoing, many studies have been conducted on an aromatic compound and a fused polycyclic aromatic compound which are each used as a light emitting organic compound for forming an emission layer or the like. However, a compound in which emission luminance and durability are sufficiently satisfied has hardly been obtained.

In general, it is required for the light emitting organic compound for forming an emission layer or the like to have high emission quantum efficiency, and as one of the compounds having high emission quantum efficiency, a perylene compound is proposed. The perylene compound has high fluorescence quantum efficiency and is expected as a constituent material of an organic light emitting device. As specific examples in which a perylene compound is used for an organic light emitting device, there are exemplified Japanese Patent Application Laid-Open No. H09-241629, Japanese Patent Application Laid-Open No. H10-36832, Japanese Patent Application Laid-Open No. 2003-104916, and Japanese Patent Application Laid-Open No. 2005-41804.

DISCLOSURE OF THE INVENTION

An object of the present invention is to provide a novel perylene compound. Further, another object of the present invention is to provide an organic light emitting device having high light emitting efficiency and good emission color purity.

The inventors of the present invention have found that an organic light emitting device having high light emitting efficiency and good emission color purity can be obtained by using, in the organic light emitting device, a perylene compound having a specific structure for an emission layer. Thus, the present invention has been completed.

A perylene compound of the present invention is a compound represented by the following general formula (1):

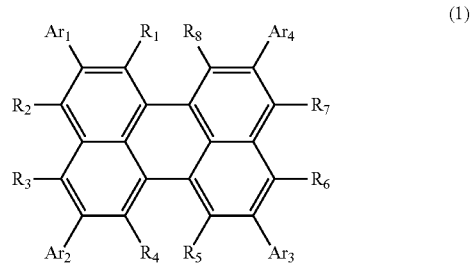

where $R_1$ to $R_8$ each represent a hydrogen atom or a substituted or unsubstituted alkyl group; and $Ar_1$ to $Ar_4$ each represent a substituent represented by the following general formula (2) or (3):

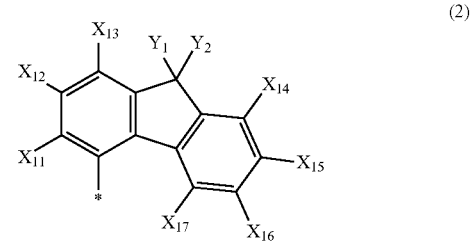

where $X_{11}$ to $X_{17}$ each represent a substituent selected from the group consisting of a hydrogen atom, a substituted or unsubstituted alkyl group, a substituted or unsubstituted aromatic hydrocarbon group, and a substituted or unsubstituted heterocyclic group, and adjacent substituents may be bonded to each other to form a ring structure; and $Y_1$ and $Y_2$ each represent a hydrogen atom or a substituted or unsubstituted alkyl group,

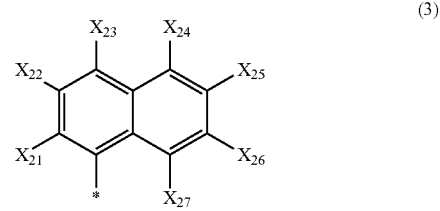

where $X_{21}$ to $X_{27}$ each represent a substituent selected from the group consisting of a hydrogen atom, a substituted or unsubstituted alkyl group, a substituted or unsubstituted aromatic hydrocarbon group, and a substituted or unsubstituted heterocyclic group, and adjacent substituents may be bonded to each other to form a ring structure.

According to the present invention, there can be provided an organic light emitting device having high light emitting efficiency and good emission color purity. Further features of the present invention will become apparent from the following description of exemplary embodiments with reference to the attached drawings.

BEST MODE FOR CARRYING OUT THE INVENTION

Figure 1:
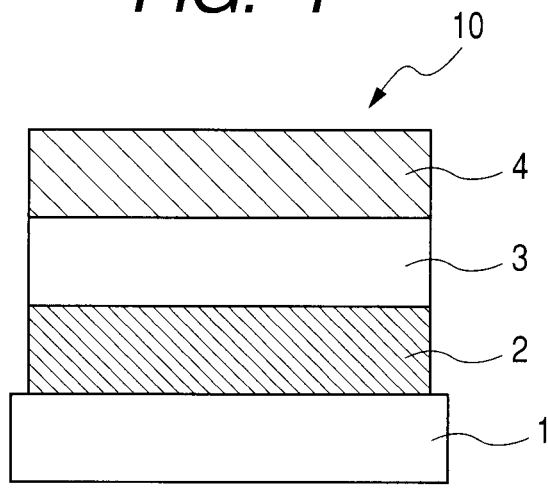
FIG. 1 is a schematic view illustrating a layer structure of a first organic light emitting device.

Hereinafter, the present invention is described in detail. First, a perylene compound of the present invention is described.

The perylene compound of the present invention is represented by the following general formula (1).

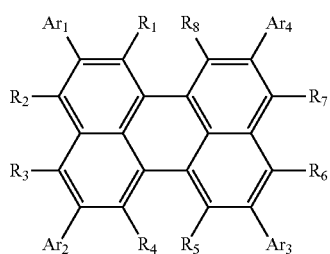

In the formula (1), $R_1$ to $R_8$ each represent a hydrogen atom or a substituted or unsubstituted alkyl group.

Specific examples of the alkyl group represented by $R_1$ to $R_8$ include, but of course are not limited to, a methyl group, an ethyl group, an n-propyl group, an iso-propyl group, an n-butyl group, an iso-butyl group, a sec-butyl group, a tert-butyl group, an n-pentyl group, a neopentyl group, an n-hexyl group, an n-octyl group, an n-decyl group, an n-dodecyl group, a cyclopropyl group, a cyclobutyl group, a cyclopentyl group, a cyclohexyl group, a norbornyl group, and an adamantyl group.

Examples of the substituent which the alkyl group may further have include, but of course are not limited to, alkyl groups such as a methyl group, an ethyl group, and a propyl group; aromatic hydrocarbon groups such as a phenyl group, a phenanthryl group, and a fluorenyl group; heterocyclic groups such as a thienyl group, a pyrrolyl group, and a pyridyl group; substituted amino groups such as a dimethylamino group, a diethylamino group, a dibenzylamino group, a diphenylamino group, a ditolylamino group, and a dianisolylamino group; alkoxy groups such as a methoxy group and an ethoxy group; aryloxy groups such as a phenoxy group and a naphthoxy group; halogen atoms such as fluorine, chlorine, bromine, and iodine; a hydroxyl group; a cyano group; and a nitro group.

In the formula (1), $Ar_1$ to $Ar_4$ each represent a substituent represented by the following formula (2) or (3).

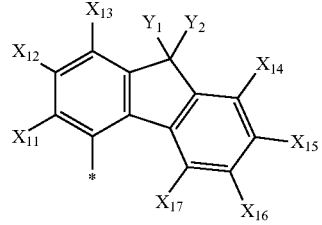

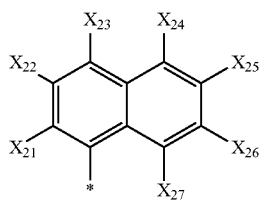

First, substituents represented by the formula (2) are described.

In the formula (2), $X_{11}$ to $X_{17}$ each represent a substituent selected from the group consisting of a hydrogen atom, a substituted or unsubstituted alkyl group, a substituted or unsubstituted aromatic hydrocarbon group, and a substituted or unsubstituted heterocyclic group.

Specific examples of the alkyl group represented by $X_{11}$ to $X_{17}$ include, but of course are not limited to, a methyl group, an ethyl group, an n-propyl group, an iso-propyl group, an n-butyl group, an iso-butyl group, a sec-butyl group, a tert-butyl group, an n-pentyl group, a neopentyl group, an n-hexyl group, an n-octyl group, an n-decyl group, an n-dodecyl group, a cyclopropyl group, a cyclobutyl group, a cyclopentyl group, a cyclohexyl group, a norbornyl group, and an adamantyl group.

Specific examples of the aromatic hydrocarbon group represented by $X_{11}$ to $X_{17}$ include, but of course are not limited to, a phenyl group, a naphthyl group, an azulenyl group, an acenaphthylenyl group, an indacenyl group, a biphenylenyl group, a fluorenyl group, an anthracenyl group, a phenanthryl group, a pyrenyl group, a chrysenyl group, a benzofluorenyl group, a tetraphenyl group, a naphthacenyl group, a triphenylenyl group, a fluoranthenyl group, a picenyl group, a pentacenyl group, a perylenyl group, and a benzofluoranthenyl group.

Specific examples of the heterocyclic group represented by $X_{11}$ to $X_{17}$ include, but of course are not limited to, a pyridyl group, a pyridazyl group, a pyrimidinyl group, a pyrazinyl group, a triazyl group, a quinolyl group, an isoquinolyl group, a phthalazinyl group, a quinazolinyl group, a quinoxalinyl group, a naphthylidinyl group, an acridinyl group, a benzoquinolyl group, a phenanthrolyl group, a monoazafluorenyl group, a diazafluorenyl group, a phenadinyl group, a pyrrolyl group, a pyrazolyl group, an imidazolyl group, a triazolyl group, an indolyl group, an indolizinyl group, a benzoimidazolyl group, a carbazolyl group, a benzocarbazolyl group, a thienyl group, a benzothienyl group, a dibenzothienyl group, a furyl group, a benzofuryl group, an isobenzofuryl group, a dibenzofuryl group, an oxazolyl group, an isoxazolyl group, a benzoxazolyl group, an oxadiazolyl group, a triazolyl group, an isothiazolyl group, a benzothiazolyl group, and a thiadiazolyl group.

Examples of the substituent which the alkyl groups, the aromatic hydrocarbon groups, and the heterocyclic groups may further have include, but are of course not limited to, alkyl groups such as a methyl group, an ethyl group, and a propyl group; aromatic hydrocarbon groups such as a phenyl group, a phenanthryl group, and a fluorenyl group; heterocyclic groups such as a thienyl group, a pyrrolyl group, and a pyridyl group; substituted amino groups such as a dimethylamino group, a diethylamino group, a dibenzylamino group, a diphenylamino group, a ditolylamino group, and a dianisolylamino group; alkoxy groups such as a methoxy group and an ethoxy group; aryloxy groups such as a phenoxy group and a naphthoxy group; halogen atoms such as fluorine, chlorine, bromine, and iodine; a hydroxyl group; a cyano group; and a nitro group.

Of the substituents represented by $X_{11}$ to $X_{17}$, adjacent substituents may be bonded to each other to form a ring structure. A benzene ring or the like is given as a specific example of the ring structure.

In the formula (2), $Y_1$ and $Y_2$ each represent a hydrogen atom or a substituted or unsubstituted alkyl group.

Specific examples of the alkyl group represented by $Y_1$ and $Y_2$ include, but of course are not limited to, a methyl group, an ethyl group, an n-propyl group, an iso-propyl group, an n-butyl group, an iso-butyl group, a sec-butyl group, a tert-butyl group, an n-pentyl group, a neopentyl group, an n-hexyl group, an n-octyl group, an n-decyl group, an n-dodecyl group, a cyclopropyl group, a cyclobutyl group, a cyclopentyl group, a cyclohexyl group, a norbornyl group, and an adamantyl group.

Examples of the substituent which the alkyl group may further have include, but of course are not limited to, alkyl groups such as a methyl group, an ethyl group, and a propyl group; aromatic hydrocarbon groups such as a phenyl group, a phenanthryl group, and a fluorenyl group; heterocyclic groups such as a thienyl group, a pyrrolyl group, and a pyridyl group; substituted amino groups such as a dimethylamino group, a diethylamino group, a dibenzylamino group, a diphenylamino group, a ditolylamino group, and a dianisolylamino group; alkoxy groups such as a methoxy group and an ethoxy group; aryloxy groups such as a phenoxy group and a naphthoxy group; halogen atoms such as fluorine, chlorine, bromine, and iodine; a hydroxyl group; a cyano group; and a nitro group.

The substituent (fluorenyl group) represented by the formula (2) is preferably a fluorenyl group represented by the following general formula (4).

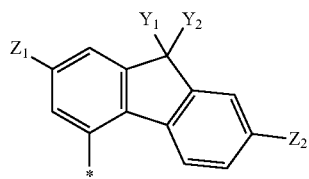

(4)

In the formula (4), $Y_1$, $Y_2$, $Z_1$, and $Z_2$ each represent a hydrogen atom or a substituted or unsubstituted alkyl group.

Specific examples of the alkyl groups represented by $Y_1$ and $Y_2$ and the substituent that the alkyl groups may further have are the same as those of $Y_1$ and $Y_2$ in the formula (2).

Specific examples of the alkyl groups represented by $Z_1$ and $Z_2$ and the substituent that the alkyl groups may further have are the same as those of $Y_1$ and $Y_2$ in the formula (2).

Next, substituents represented by the formula (3) are described.

In the formula (3), $X_{21}$ to $X_{27}$ each represent a substituent selected from the group consisting of a hydrogen atom, a substituted or unsubstituted alkyl group, a substituted or unsubstituted aromatic hydrocarbon group, and a substituted or unsubstituted heterocyclic group.

Specific examples of the alkyl group represented by $X_{21}$ to $X_{27}$ include, but of course are not limited to, a methyl group, an ethyl group, an n-propyl group, an iso-propyl group, an n-butyl group, an iso-butyl group, a sec-butyl group, a tert-butyl group, an n-pentyl group, a neopentyl group, an n-hexyl group, an n-octyl group, an n-decyl group, an n-dodecyl group, a cyclopropyl group, a cyclobutyl group, a cyclopentyl group, a cyclohexyl group, a norbornyl group, and an adamantyl group.

Specific examples of the aromatic hydrocarbon group represented by $X_{21}$ to $X_{27}$ include, but of course are not limited to, a phenyl group, a naphthyl group, an azulenyl group, an acenaphthylenyl group, an indacenyl group, a biphenylenyl group, a fluorenyl group, an anthracenyl group, a phenanthryl group, a pyrenyl group, a chrysenyl group, a benzofluorenyl group, a tetraphenyl group, a naphthacenyl group, a triphenylenyl group, a fluoranthenyl group, a picenyl group, a pentacenyl group, a perylenyl group, and a benzofluoranthenyl group.

Specific examples of the heterocyclic group represented by $X_{21}$ to $X_{27}$ include, but of course are not limited to, a pyridyl group, a pyridazyl group, a pyrimidinyl group, a pyrazinyl group, a triazyl group, a quinolyl group, an isoquinolyl group, a phthalazinyl group, a quinazolinyl group, a quinoxalinyl group, a naphthylidinyl group, an acridinyl group, a benzoquinolyl group, a phenanthrolyl group, a monoazafluorenyl group, a diazafluorenyl group, a phenadinyl group, a pyrrolyl group, a pyrazolyl group, an imidazolyl group, a triazolyl group, an indolyl group, an indolizinyl group, a benzoimidazolyl group, a carbazolyl group, a benzocarbazolyl group, a thienyl group, a benzothienyl group, a dibenzothienyl group, a furyl group, a benzofuryl group, an isobenzofuryl group, a dibenzofuryl group, an oxazolyl group, an isoxazolyl group, a benzoxazolyl group, an oxadiazolyl group, a triazolyl group, an isothiazolyl group, a benzothiazolyl group, and a thiadiazolyl group.

Examples of the substituent which the alkyl groups, the aromatic hydrocarbon groups, and the heterocyclic groups may further have include, but are of course not limited to, alkyl groups such as a methyl group, an ethyl group, and a propyl group; aromatic hydrocarbon groups such as a phenyl group, a phenanthryl group, and a fluorenyl group; heterocyclic groups such as a thienyl group, a pyrrolyl group, and a pyridyl group; substituted amino groups such as a dimethylamino group, a diethylamino group, a dibenzylamino group, a diphenylamino group, a ditolylamino group, and a dianisolylamino group; alkoxy groups such as a methoxy group and an ethoxy group; aryloxy groups such as a phenoxy group and a naphthoxy group; halogen atoms such as fluorine, chlorine, bromine, and iodine; a hydroxyl group; a cyano group; and a nitro group.

Of the substituents represented by $X_{21}$ to $X_{27}$, adjacent substituents may be bonded to each other to form a ring structure. Specific examples of the ring structure include a benzene ring and a naphthalene ring.

The substituent (naphthyl group) represented by the formula (3) is preferably a naphthyl group represented by the following general formula (5):

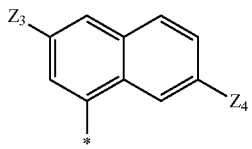

(5)

where $Z_3$ and $Z_4$ each represent a hydrogen atom or a substituted or unsubstituted alkyl group.

Specific examples of the alkyl groups represented by $Z_3$ and $Z_4$ and the substituent that the alkyl groups may further have are the same as those of $Y_1$ and $Y_2$ in the formula (2).

In the perylene compound represented by the formula (1), it is particularly preferred that the substituents $Ar_1$ to $Ar_4$ all represent a fluorenyl group represented by the formula (4) or that the substituents $Ar_1$ to $Ar_4$ all represent a naphthyl group represented by the formula (5).

Next, a synthesis method of the perylene compound of the present invention is described.

The perylene compound of the present invention can be synthesized by Suzuki-Miyaura coupling reaction using a boronic acid ester (P-Bpin$_4$), a halogen compound (Ar—X), and a tetrakis(triphenylphosphine)palladium catalyst, the coupling reaction being shown in the following formula (6). It should be noted that boronic acid ester, P-Bpin$_4$, can be synthesized with reference to a synthesis method described in Chem. Commn., 2005, 16, 2172.

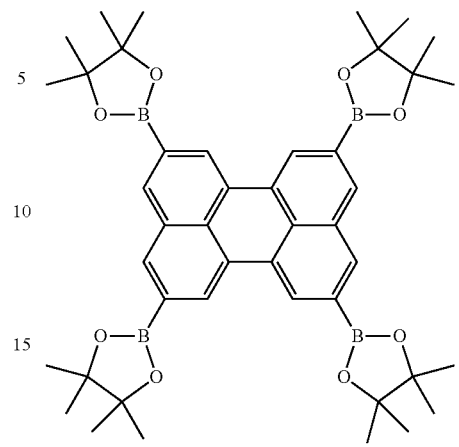

P-Bpin$_4$

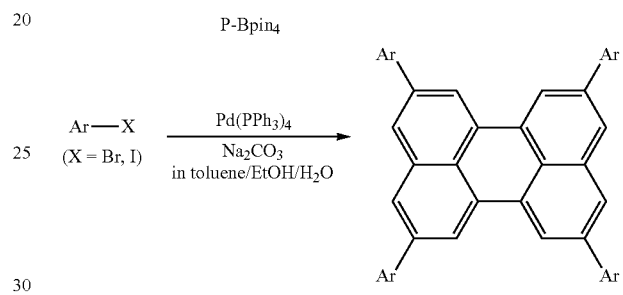

Hereinafter, specific structural formulae of the perylene compound of the present invention are shown below, but the present invention is, of course, not limited to those.

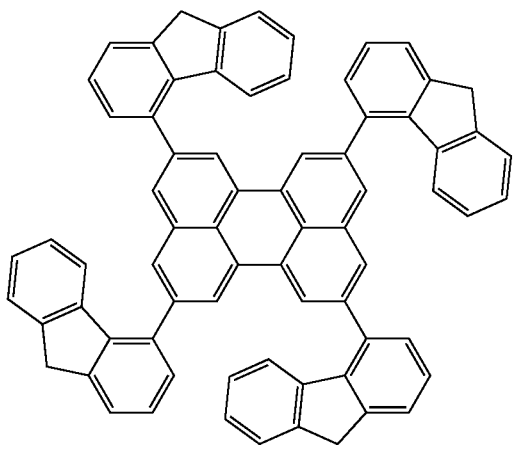

P101

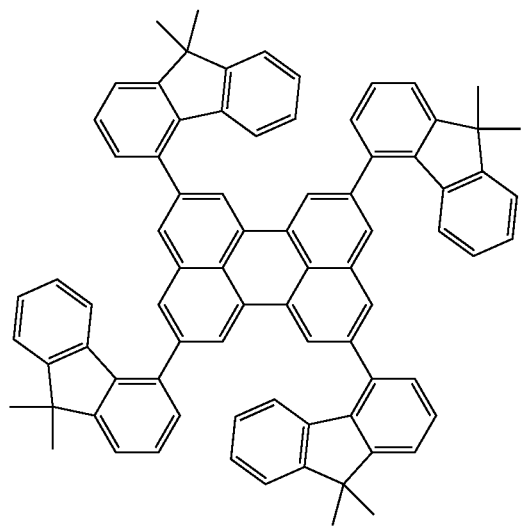

P102

-continued
P103
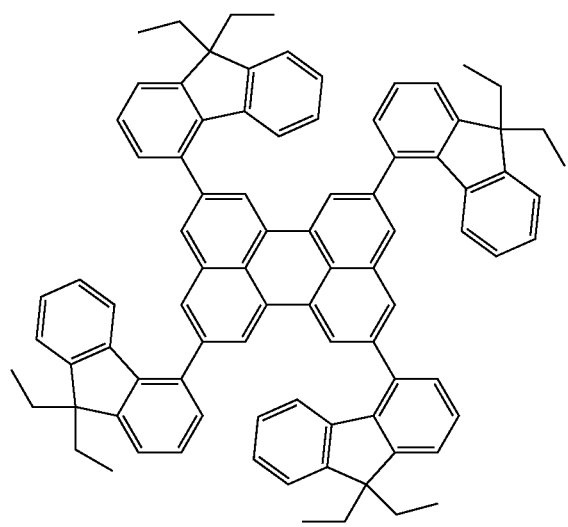
P104
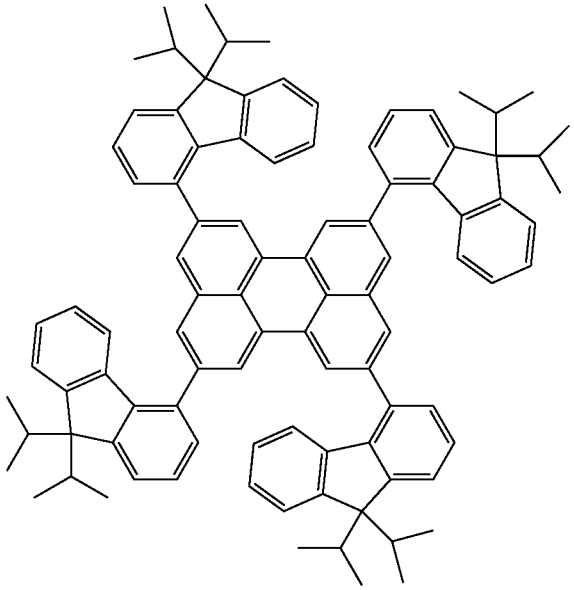
P105
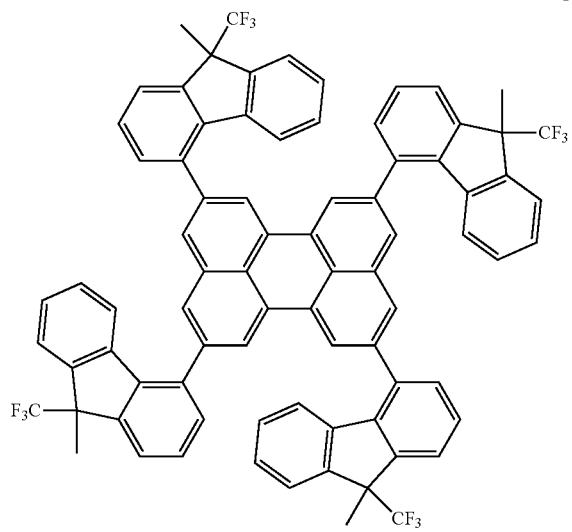
P106
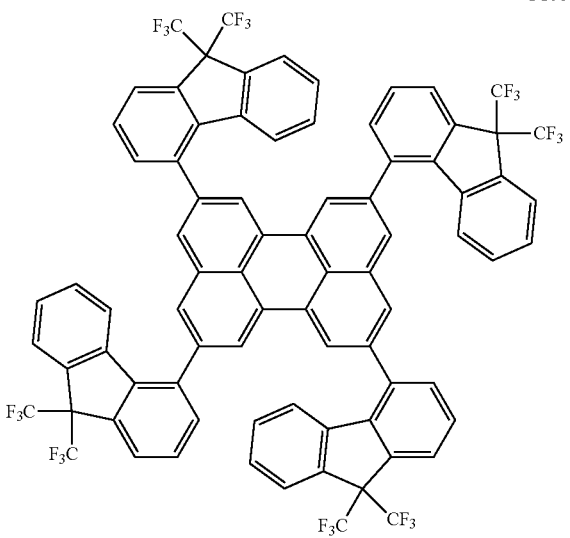
P107
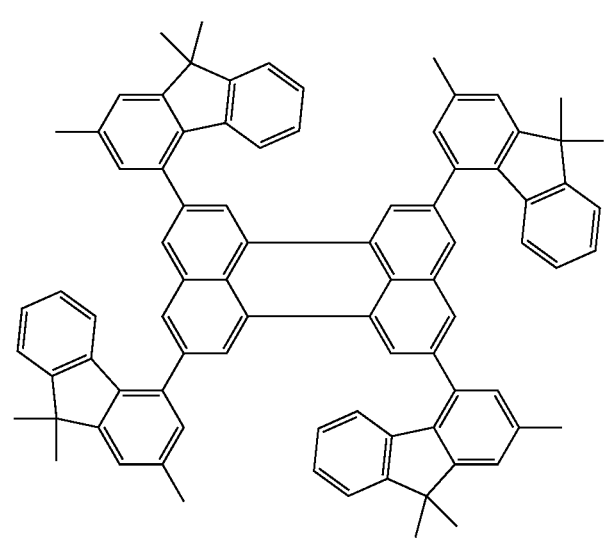

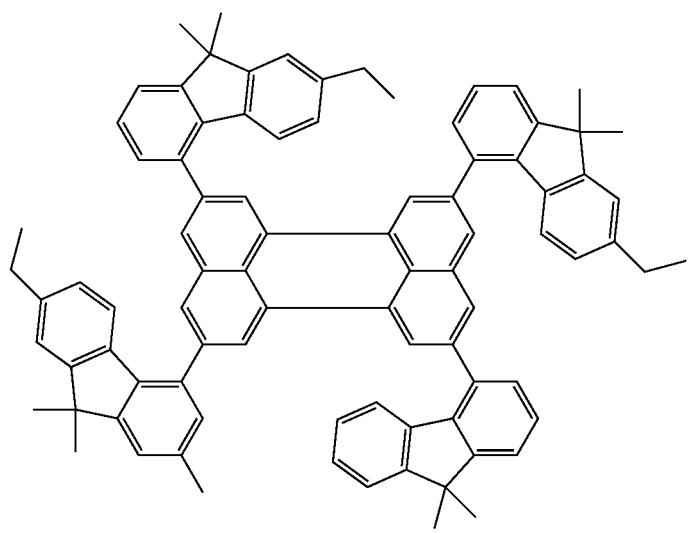
P108
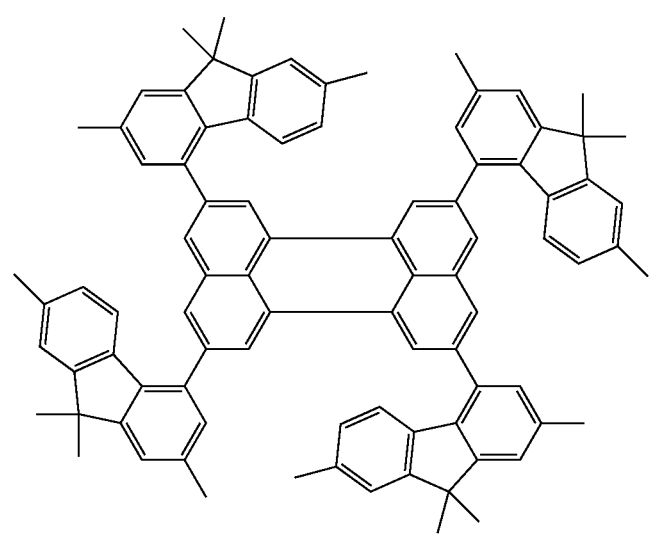
P109
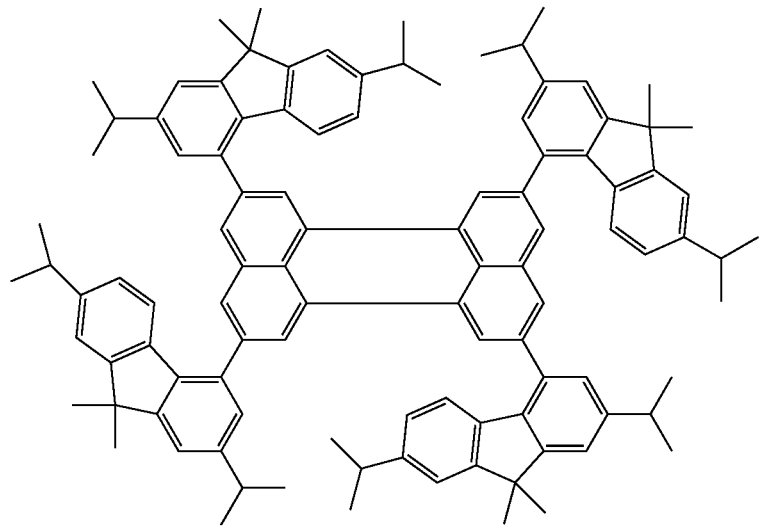
P110

P111
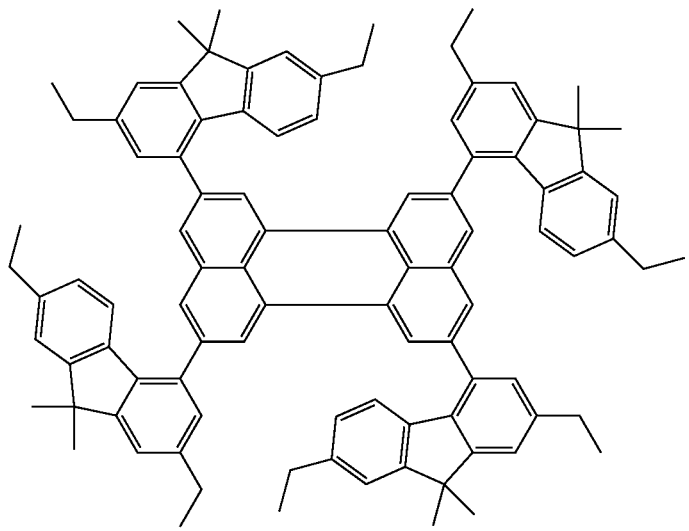
P112
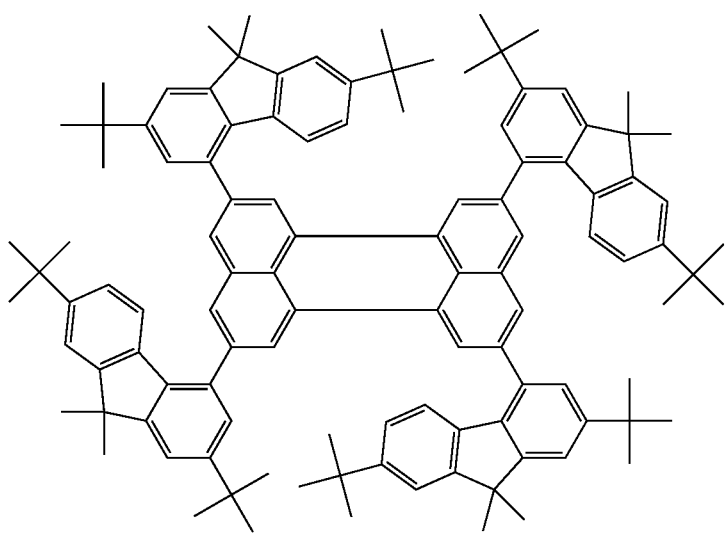
P201
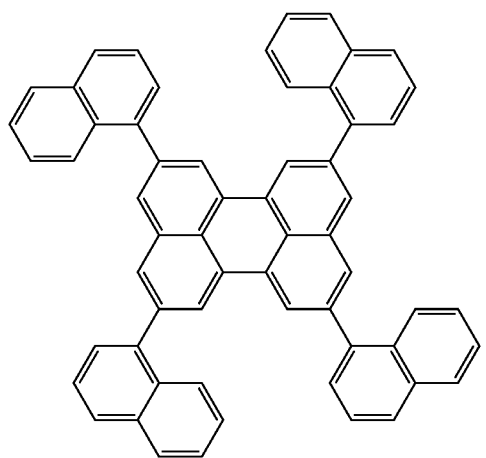
P202
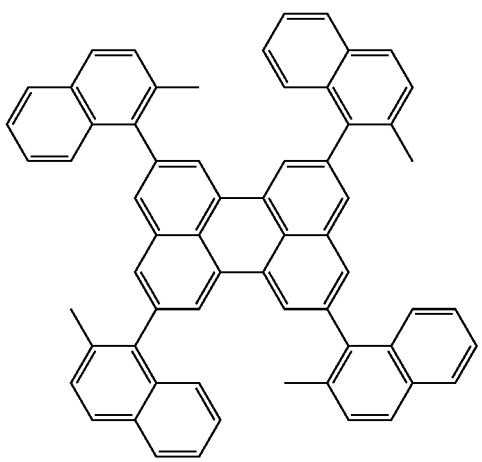

-continued
P203
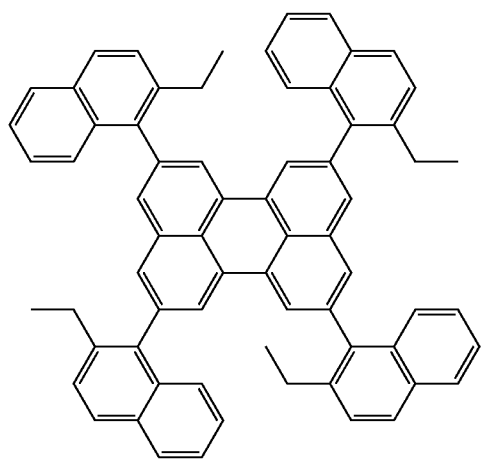
P204
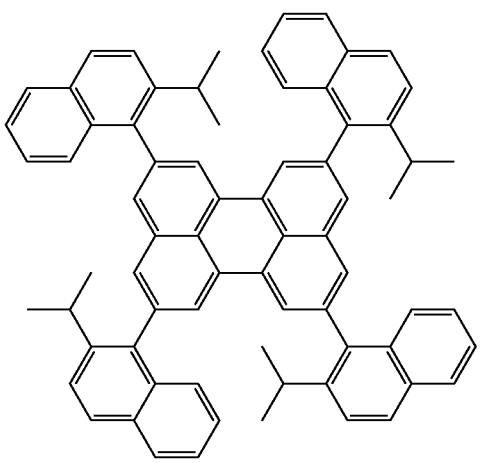
P205
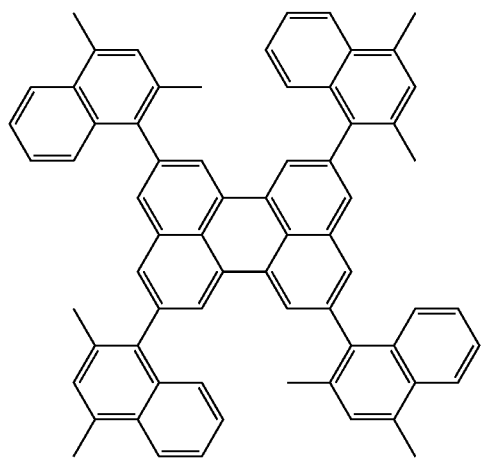
P206
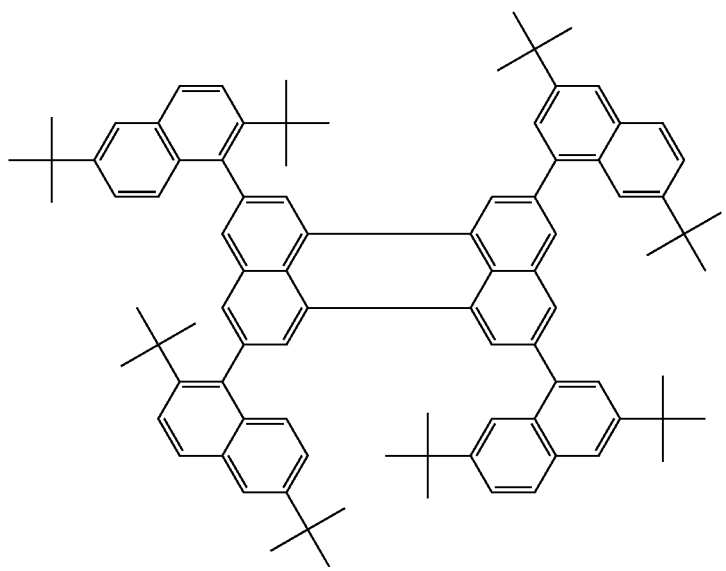

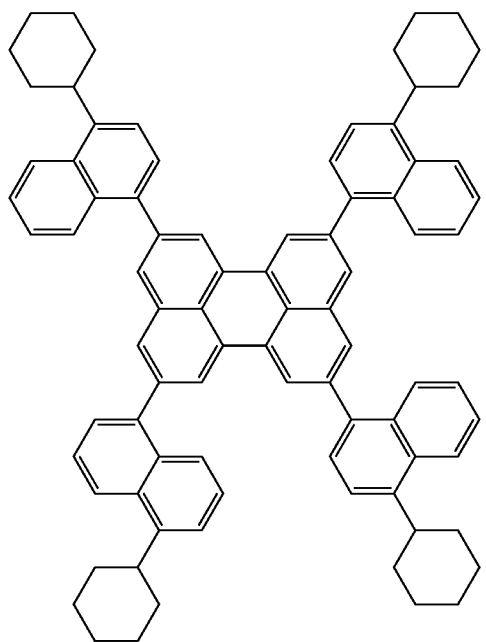
P207
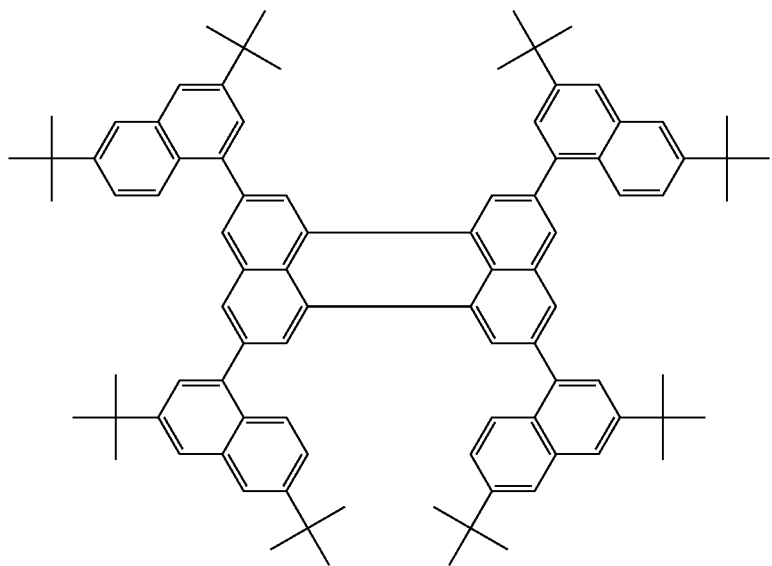
P208

-continued
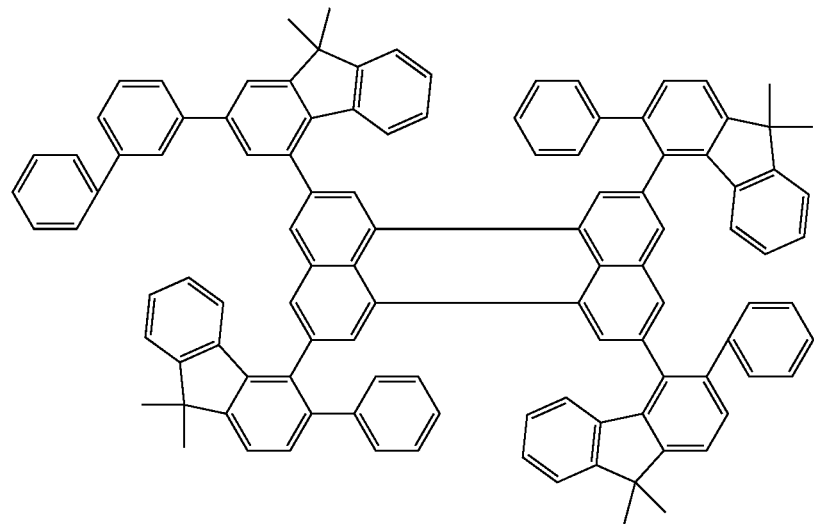
P301
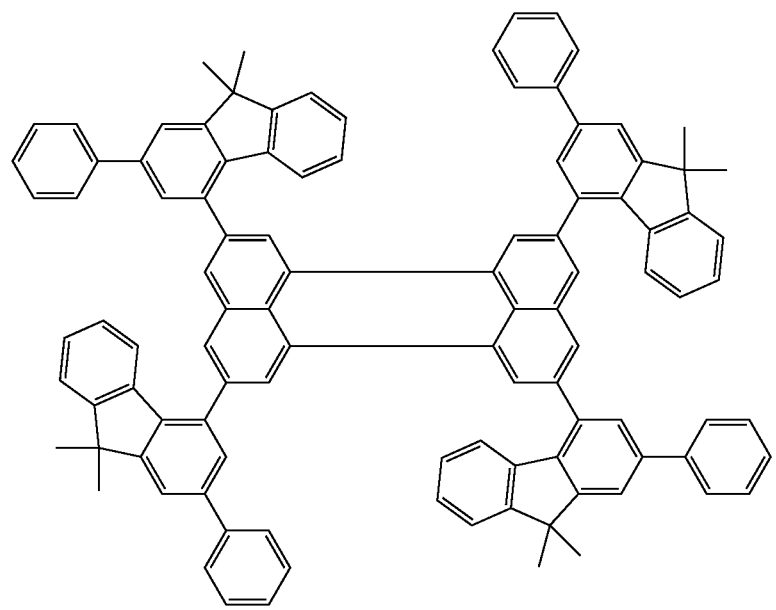
P302

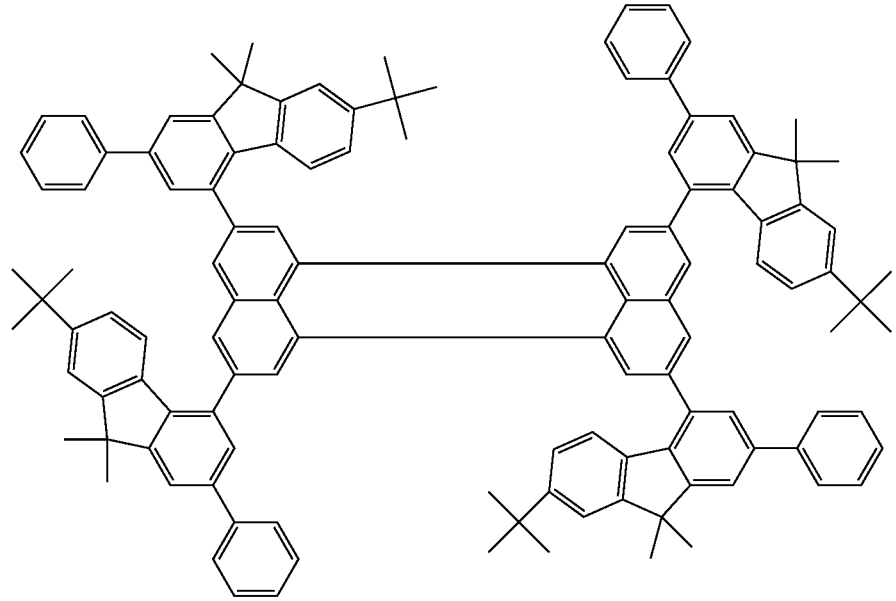
P303
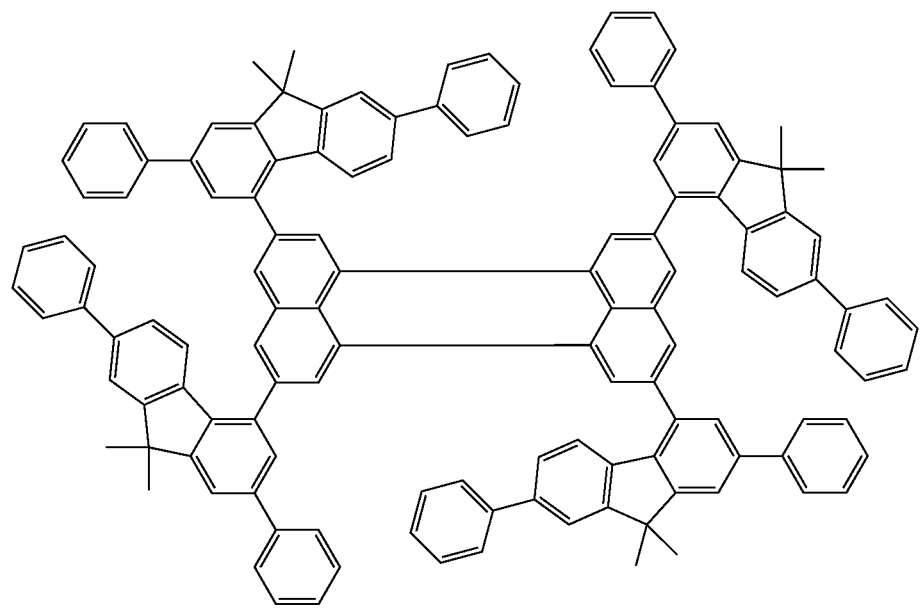
P304

-continued
P305
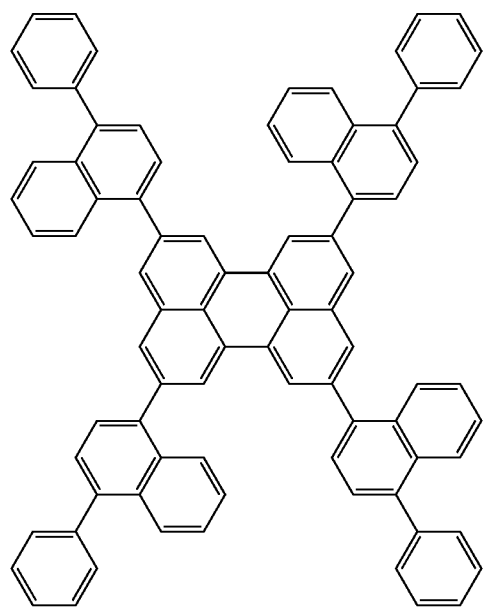
P306
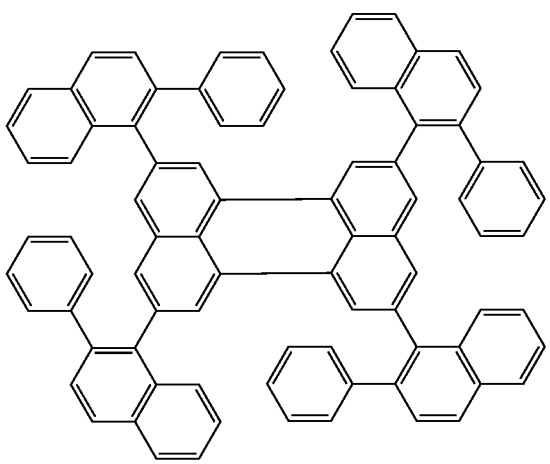
P307
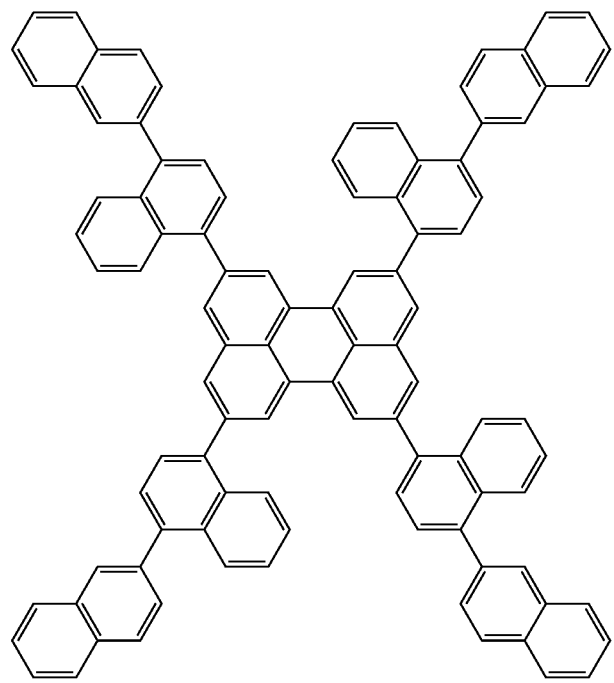

-continued
P308
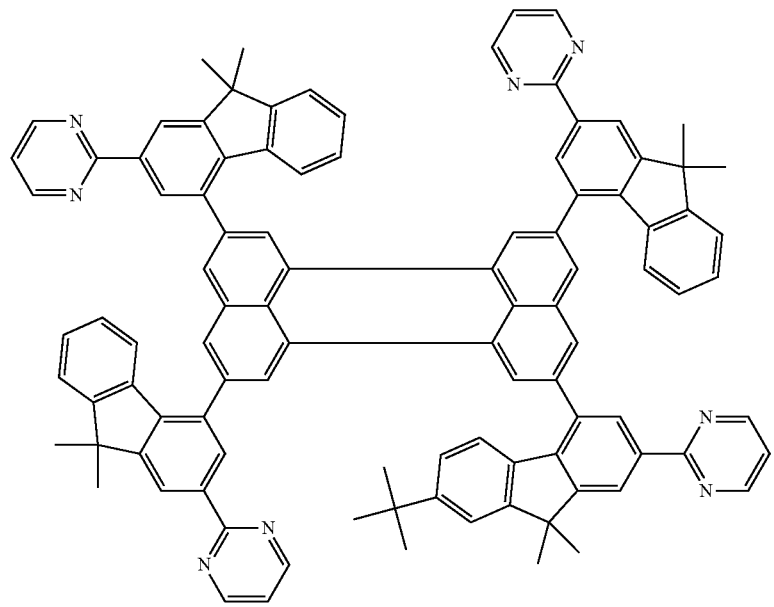
P309
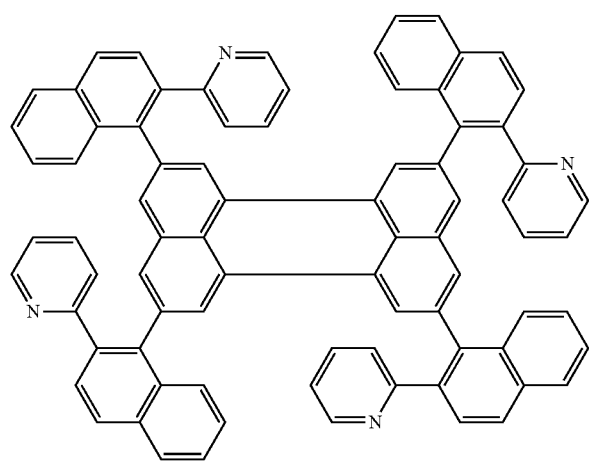
P401
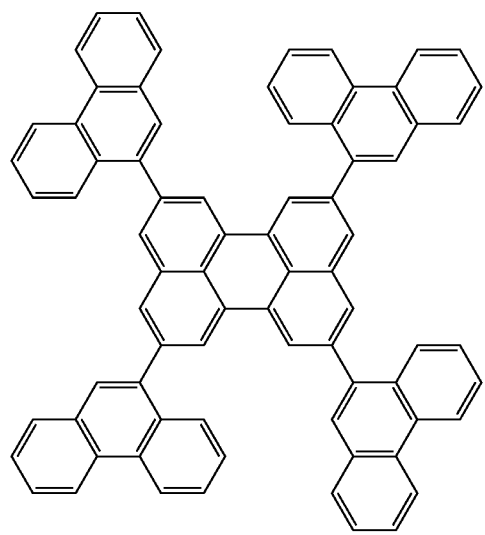
P402
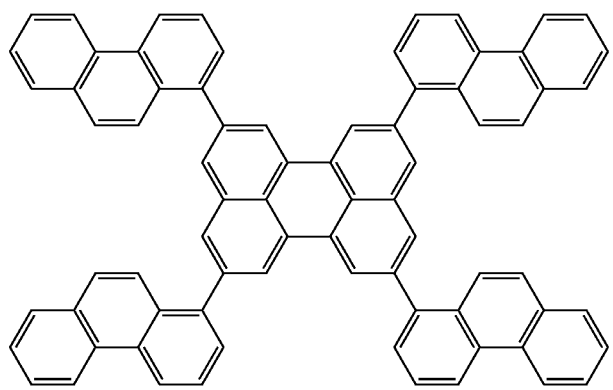

-continued
P403
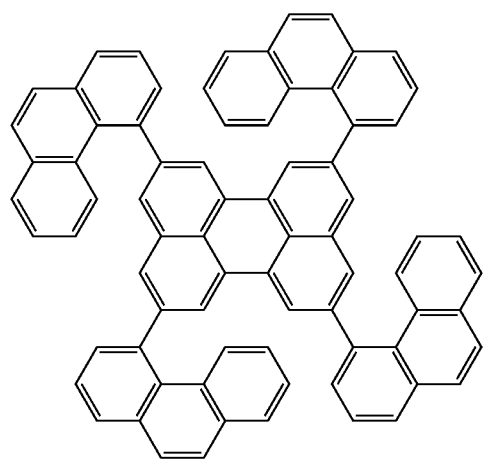
P404
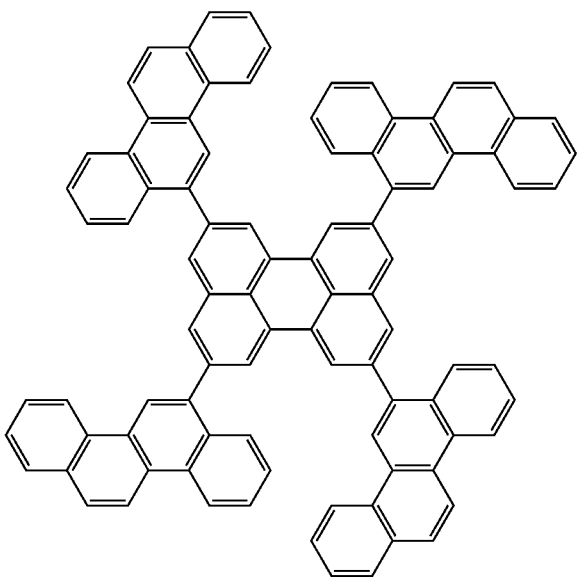
P405
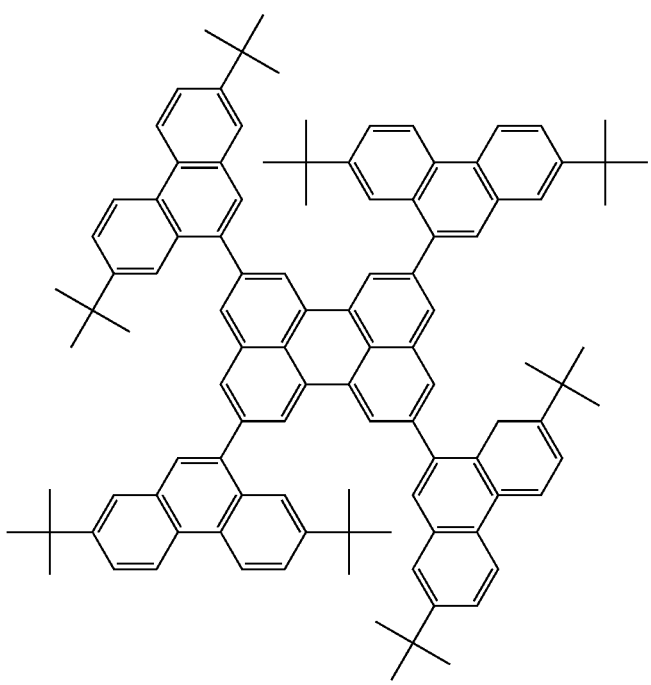

-continued
P406
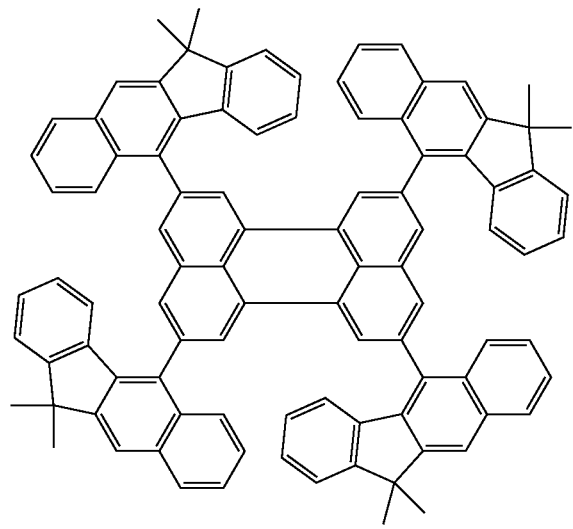
P407
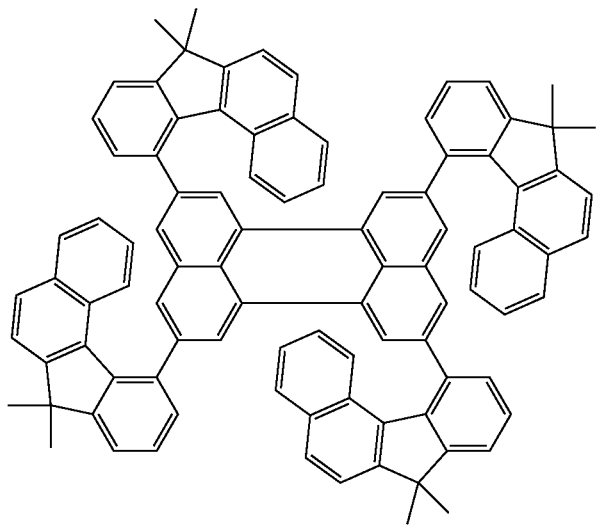
P408
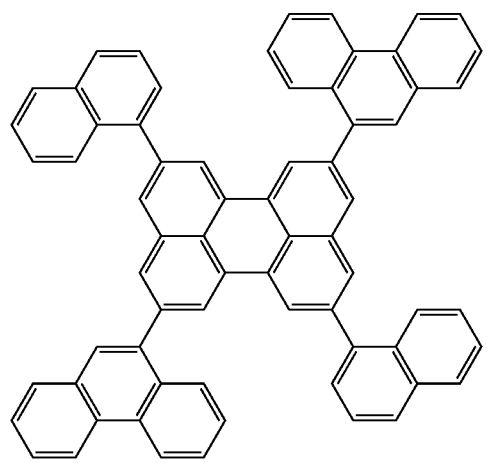
P409
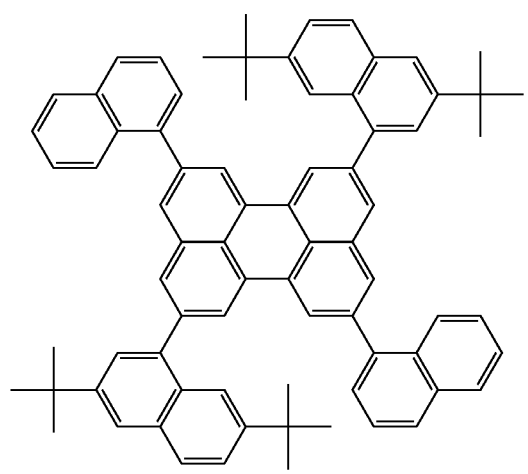

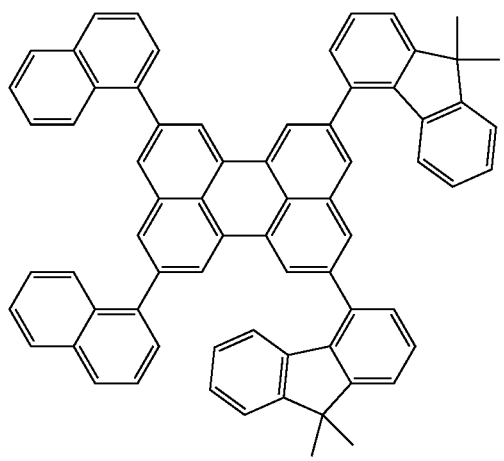

P410

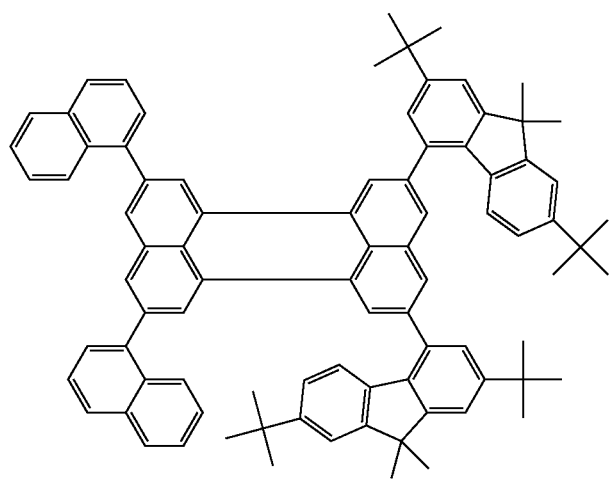

P411

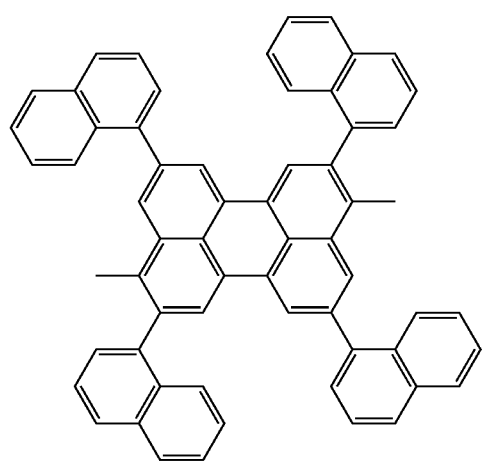

P412

Next, the organic light emitting device of the present invention is described in detail.

The organic light emitting device of the present invention includes an anode, a cathode, and an organic compound layer which is sandwiched between the anode and the cathode. In the organic light emitting device of the present invention, one of the anode and the cathode is transparent or semi-transparent. The organic light emitting device of the present invention is preferably an electric field light emitting device which emits light by applying a voltage between the anode and the cathode.

The organic compound layer may be formed of a single layer or multiple layers.

A first layer structure of the organic light emitting device is specifically as follows: a substrate, an anode, an emission layer, and a cathode are laminated in the stated order.

A second layer structure is as follows: a substrate, an anode, a hole transport layer, an electron transport layer, and a cathode are laminated in the stated order. In this case, when an interface of the hole transport layer and the electron transport layer emits light, the both layers can be regarded as the emission layers.

A third layer structure is as follows: a substrate, an anode, a hole transport layer, an emission layer, an electron transport layer, and a cathode are laminated in the stated order.

FIG. 1 shows one example of a layer structure of first organic light emitting device 10. In FIG. 1, the organic light emitting device 10 includes a substrate 1 formed of, for example, glass; an anode 2, an emission layer 3, and a cathode 4. The anode 2 is, for example, a reflection side electrode and the anode itself is a transparent electrode having a reflective member. When the anode 2 is a reflection side electrode, the cathode 4 is a light extraction side electrode. In this case, the cathode is a light transmissive electrode such as ITO.

Figure 2:
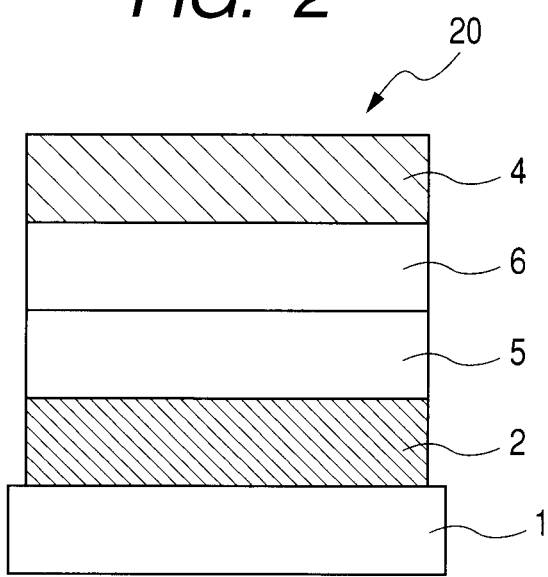
FIG. 2 is a schematic view illustrating a layer structure of a second organic light emitting device.

FIG. 2 shows a layer structure of a second organic light emitting device 20. FIG. 2 is the same as FIG. 1 except that the emission layer 3 is not provided and a hole transport layer 5 and an electron transport layer 6 are provided between the anode 2 and the cathode 4 stated order from the anode side.

Figure 3:
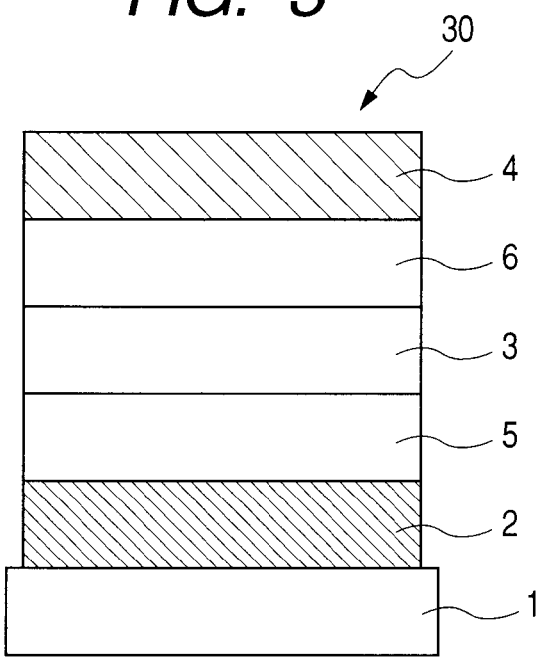
FIG. 3 is a schematic view illustrating a layer structure of a third organic light emitting device.

FIG. 3 shows a layer structure of a third organic light emitting device 30. FIG. 3 is the same as FIG. 1 except that a hole transport layer 5 is provided between the anode 2 and the emission layer 3 and an electron transport layer 6 is provided between the emission layer 3 and the cathode 4.

In the third layer structure, a layer (hole/exciton blocking layer) which inhibits a hole or an exciton from migrating out to a cathode side may be inserted between the emission layer and the electron transport layer. When a compound having extremely high ionization potential is used as a constituent material of the hole blocking layer or the exciton blocking layer, it is effective for improving the light emitting efficiency.

However, those first to third layer structures are each only a basic device structure, and the structure of the organic light emitting device of the present invention is not limited to those. There can be given various layer structures, for example: an insulating layer, an adhesive layer, or an interference layer is provided at an interface of an electrode and an organic layer; a hole transport layer is formed of two layers having different ionization potentials; and an emission layer has a laminated structure formed of two layers or more.

In the organic light emitting device of the present invention, an organic compound layer contains at least one kind of perylene compound of the present invention. At that time, one kind of perylene compound of the present invention or two or more kinds of perylene compounds of the present invention may be contained in one layer.

Here, the organic compound layer containing the perylene compound of the present invention specifically includes the emission layer, the hole transport layer, and the electron transport layer, each of which is used for one of the first to third layer structures, and preferably includes the emission layer.

Further, the emission layer may be formed of the perylene compound of the present invention alone, and it is preferably formed of a host and a guest. The perylene compound of the present invention may be used as the host or as the guest, and is preferably used as the guest.

The guest used herein is a compound which plays a role of main light emission inside the emission layer. On the other hand, the host is a compound which is present as a matrix in the periphery of the guest inside the emission layer, and mainly plays roles of transporting carriers and donating excitation energy to the guest.

Here, the concentration of the guest with respect to the host is 0.01 wt % to 50 wt % and preferably 0.1 wt % to 20 wt % based on the total amount of the constituent materials of the emission layer. From the viewpoint of preventing concentration quenching, the concentration of the guest is more preferably 10 wt % or less with respect to the total amount of the constituent materials of the emission layer. Further, the guest may be uniformly included throughout the emission layer, may be included in the emission layer with a concentration gradient existing, or may be partially included in a certain area to form an area formed only of the host where no guest is included.

In order to increase the light emitting efficiency of the organic light emitting device, it goes without saying that the emission quantum efficiency of a main light-emitting material itself needs to be increased.

By the way, the perylene compound is known as one of the compounds having high emission quantum efficiency. However, in the perylene compound, a perylene ring, which is a basic skeleton, has a large π-conjugate plane, and hence, an intermolecular interaction by the π-conjugate plane is strong. For this reason, the intermolecular stacking in the perylene compound is remarkable. Consequently, when the perylene compound is used as a constituent material of an organic light emitting device, particularly as a guest of an emission layer, concentration quenching occurs due to the intermolecular stacking, and the light emitting efficiency decreases remarkably. Further, excimer emission becomes remarkable due to the intermolecular stacking, and the long wavelength component of the emission spectrum increases. Therefore, the emission color purity of the device deteriorates.

In order to prevent the above-mentioned decrease in the light emitting efficiency and deterioration of the color purity, a highly sterically-hindered group needs to be introduced into the perylene ring for the purpose of reducing the intermolecular stacking between the perylene rings. However, HOMO (Highest Occupied Molecular Orbital) and LUMO (Lowest Unoccupied Molecular Orbital), which are directly involved in an emission process, are localized on the perylene ring, and hence, when a substituent having an $sp_3$ carbon atom, such as an alkyl group, is directly bonded to the perylene ring, the perylene ring becomes energetically unstable and may cause degradation of light emission. Therefore, the highly sterically-hindered group is preferably an aryl group.

In the case of substituting an aryl group as the highly sterically-hindered group, the substitution position therefor is a position where the increase of π-conjugate length becomes small, specifically, is preferably 2-, 5-, 8-, or 11-position of the perylene ring. On the other hand, when an aryl group is introduced into 3-, 4-, 9-, or 10-position, i.e., peri-position, of the perylene ring, the increase of π-conjugate length is remarkable and the band gap of the perylene compound itself becomes excessively narrow. Accordingly, it may become difficult to use the organic light emitting device of the present invention as a blue or green light emitting device.

As the aryl group used as the highly sterically-hindered group, a fused polycyclic aromatic group is preferably given, in which the dihedral angle with respect to the plane including the perylene ring is large and the rigidity of the group to become steric hindrance is high. Specific examples thereof include a fluorene-4-yl group and a naphthalene-1-yl group. Those fused polycyclic aromatic groups each have a larger excluded volume effect and a higher thermal stability as compared with a sterically-hindered group having a rotatable position and having a high mobility like an ortho-biphenyl group.

The perylene compound of the present invention which is molecularly designed taking the above into consideration can effectively reduce the intermolecular stacking which may occur in the light emitting device, while maintaining the original emission color (blue) of perylene without narrowing the band gap. Accordingly, when the perylene compound of the present invention is used as a constituent material of a blue light emitting device, specifically, as a guest of an emission layer, an organic light emitting device having high light emitting efficiency and good color purity can be obtained.

By the way, the perylene compound of the present invention can be used as a constituent material of a green light emitting device, specifically, as a host of an emission layer. The above-mentioned intermolecular stacking can be observed not only between guests, but also between hosts. Here, when the intermolecular stacking occurs between hosts, an excimer is formed between the hosts. As a result, it becomes less likely that the transfer of excitation energy from the host to the guest is performed effectively, which leads to the decrease in the light emitting efficiency of the organic light emitting device. On the other hand, in the perylene compound of the present invention, a specific aryl group, which is a highly sterically-hindered group, is substituted in the perylene ring. As a result, the intermolecular stacking is reduced, and hence, even when the perylene compound is used as a host of an emission layer, excitation energy is transferred effectively to the guest and a green light emitting device having high light emitting efficiency can be obtained.

As described above, the perylene compound of the present invention can be used as the guest and the host of an emission layer, but the application of the perylene compound of the present invention is not limited to those. Specifically, the perylene compound of the present invention may be used as a constituent material of a green light emitting device, specifically, as a guest of an emission layer, a constituent material of an electron transport layer, or the like.

In the organic light emitting device of the present invention, there can be used together the following conventionally known compound as required, in addition to the perylene compound of the present invention: a low-molecular or high-molecular hole transporting compound, a light emitting compound, an electron transporting compound, or the like.

Those compounds are exemplified below.

A hole injecting/transporting material preferably is a material having a high hole mobility to facilitate the injection of a hole from an anode and to transport the injected hole to an emission layer. As low-molecular and high-molecular materials having hole injecting/transporting abilities include, but are not limited to, a triarylamine derivative, a phenylene diamine derivative, a stilbene derivative, a phthalocyanine derivative, a porphyrin derivative, poly(vinylcarbazole), poly(thiophene), and other conductive polymers.

As the light emitting material mainly involved in the light emitting function, in addition to the above perylene compounds, there are given, but of course the host is not limited to, fused ring compounds (such as fluorene derivatives, pyrene derivatives, tetracene derivatives, 9,10-diphenylanthracene derivatives, and rubrene); quinacridone derivatives; cumarin derivatives; stylbene derivatives; organic aluminum complexes such as tris(8-quinolilato)aluminum; organic beryllium complexes; phosphorescent organometallic complexes (such as iridium complexes and platinum complexes); and polymer derivatives such as poly(phenylene vinylene) derivatives, poly(fluorene) derivatives, and poly(phenylene) derivatives.

The electron injecting/transporting material may be arbitrarily selected from compounds each of which facilitates the injection of an electron from a cathode and is capable of transporting the injected electron to the emission layer. In addition, the material is selected in consideration of, for example, a balance with the hole mobility of the hole injecting/transporting material. The materials having electron injecting/transporting abilities include, but are of course not limited to, an oxadiazole derivative, an oxazole derivative, a pyrazine derivative, a triazole derivative, a triazine derivative, a quinoline derivative, a quinoxaline derivative, a phenanthroline derivative, and an organic aluminum complexes.

As a material for constituting an anode, a material having as large a work function as possible is preferred. Examples of available materials include: metal elements such as gold, platinum, silver, copper, nickel, palladium, cobalt, selenium, vanadium, and tungsten, and alloys thereof; and metal oxides such as tin oxide, zinc oxide, indium oxide, indium tin oxide (ITO), and indium zinc oxide. Further, conductive polymers such as polyaniline, polypyrrole, and polythiophene may also be used. Each of those electrode substances may be used singly. Alternatively, two kinds or more of them may also be used in combination. Further, the anode may adopt any one of a single layer construction and a multilayer construction.

On the other hand, as a material constituting a cathode, a material having as small a work function as possible is preferred. Examples of available materials include: alkali metals such as lithium, alkali earth metals such as calcium, and metal elements such as aluminum, titanium, manganese, silver, lead, and chromium. Alternatively, alloys in combination of those metal elements may also be used. For example, magnesium-silver, aluminum-lithium, and aluminum-magnesium can be used. Metal oxides such as indium tin oxide (ITO) may also be used. One kind of those electrode substances may be used alone or a combination of two kinds or more may be used. Further, the cathode may adopt any one of a single layer construction and a multilayer construction.

Substrates which are used in the organic light emitting device of the present invention include: opaque substrates such as metallic substrates and ceramics substrates; and transparent substrates such as glass, quartz, and plastic sheet substrates, but are not particularly limited to these materials. In addition, a color filter film, a fluorescent color converting filter film, a dielectric reflection film, or the like may be used in the substrate to control emission light.

It should be noted that, a protective layer or a sealing layer may be formed on the prepared device to prevent the device from contacting oxygen, moisture, or the like. The protective layer may include a diamond thin film, a film made of an inorganic material such as metal oxide or metal nitride, a polymer film made of a fluorine resin, polyethylene, a silicone resin, a polystyrene resin, or the like, or may include a photo-curing resin or the like. Further, the device itself can be covered with glass, a gas-impermeable film, a metal, or the like and packaged with an appropriate sealing resin.

Moreover, with respect to a direction of extracting light of the device, both a bottom emission structure (structure in which light is extracted from the substrate side) and a top emission structure (structure in which light is extracted from a side opposite to the substrate) can be acceptable.

In the organic light emitting device of the present invention, a layer containing the perylene compound of the present invention and a layer containing another organic compound are formed by the method described below. In general, a thin film is formed by using a vacuum deposition method, ionization-assisted deposition method, a sputtering method, or a plasma method, or the thin film may be formed by dissolving the compound in a suitable solvent and subjecting the resultant to a known applying method (e.g., a spin coating method, a dipping method, a casting method, an LB method, an ink jet method, etc.). Here, when the layer is formed by the vacuum deposition method or a solution coating method, the layer hardly undergoes crystallization or the like, and is excellent in stability over time. In film formation by the coating method, the film may be formed by using a compound in combination with an appropriate binder resin.

Examples of the binder resin include, but are of course not limited to, a polyvinylcarbazole resin, a polycarbonate resin, a polyester resin, an ABS resin, an acrylic resin, a polyimide resin, a phenol resin, an epoxy resin, a silicone resin, and a urea resin. In addition, these binder resins each may be used as a homopolymer or a copolymer, and one kind of binder resin may be used alone or a mixture of two or more kinds may be used. Further, a known additive such as a plasticizer, an antioxidant, or a UV absorber, as required, may be used in combination.

The organic light emitting device of the present invention can be applied to the products which require energy saving and high luminance. Examples of the application include a display apparatus, a light source of a printer, an illuminating device, and a backlight of a liquid crystal display apparatus.

As the display apparatus, there can be exemplified an energy-saving light-weight flat panel display having high visibility.

Further, as the light source of a printer, for example, a laser light source of a laser-beam printer, which is widely used at present, can be replaced with the organic light emitting device of the present invention. As a method of replacing the laser light source, there can be exemplified a method involving placing organic light emitting devices in an array. In this case, each of the organic light emitting devices can be addressed independently. When the laser light source is replaced with the organic light emitting device of the present invention, no change is observed as compared with the conventional laser-beam printer in regard to forming an image by performing desired exposure on a photosensitive drum. Here, by using the organic light emitting device of the present invention, the volume of the apparatus can be reduced to a large extent.

As for the illuminating device and the backlight, an energy-saving effect can be expected by using the organic light emitting device of the present invention.

Figure 4:
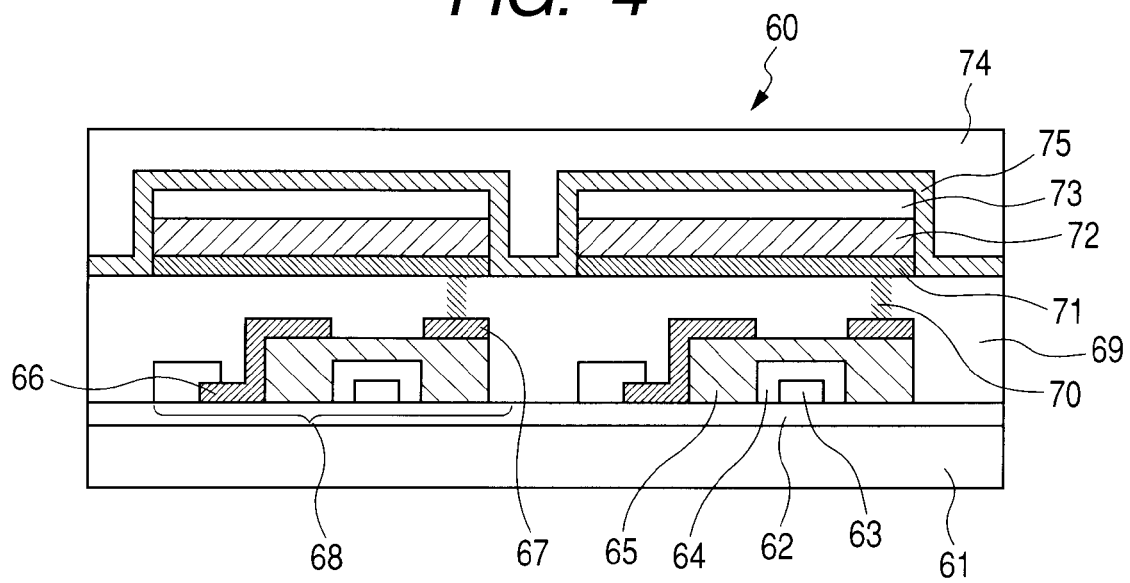
FIG. 4 is a schematic view illustrating one example of a cross-sectional structure of a TFT substrate.

FIG. 4 is a schematic view illustrating one example of a cross-sectional structure of a TFT substrate. In FIG. 1, two pairs each including an organic light emitting device and a TFT device are illustrated. The display apparatus of the present invention includes an organic light emitting device and a TFT device, in which one of an anode and a cathode of the organic light emitting device is connected to one of a source electrode and a drain electrode of the TFT device. In the embodiment of the present invention, an anode of the organic light emitting device is connected to a source electrode of the TFT device. A display apparatus 60 illustrated in FIG. 1 includes a substrate 61 made of glass or the like and a moisture-proof film 62 for protecting a member (TFT or organic compound layer) to be formed thereon. The substrate 61 is coated with the moisture-proof film 62. As a material forming the moisture-proof film 62, there are exemplified silicon oxide or a complex of silicon oxide and silicon nitride. A gate electrode 63 is provided on the moisture-proof film 62. The gate electrode 63 is fabricated by forming a metal such as Cr into a film by sputtering and being patterned into a predetermined circuit shape. Each gate electrode 63 is coated with a gate insulating film 64. Two gate insulating films 64 illustrated in FIG. 1 are placed apart from each other. The gate insulating film 64 can be obtained by forming silicon oxide or the like into a film by a plasma CVD method, a catalytic chemical vapor deposition (cat-CVD) method, or the like, and performing patterning. The gate insulating film 64 is coated with a semiconductor layer 65, and the semiconductor layer 65 is provided above the gate electrode 63. The semiconductor layer 65 can be obtained by forming a silicon film by a plasma CVD method or the like (and performing annealing in some cases at a temperature of 290° C. or higher) and performing patterning based on the circuit shape.

In addition, a drain electrode 66 and a source electrode 67 are provided on the semiconductor layer 65. The TFT device includes the gate electrode, the gate insulating film, the semiconductor layer, the drain electrode, and the source electrode. On an upper part of a TFT device 68, there is provided an insulating film 69. A contact hole (through-hole) 70 is provided in the insulating film 69. The source electrode 67 is connected with an anode 71 of the organic light emitting device via the contact hole 70.

On the anode 71, an organic compound layer 72 formed of multiple layers or a single layer and a cathode 73 are laminated sequentially. Further, as illustrated in FIG. 1, there may be provided a first protective layer 74 and a second protective layer 75 for the purpose of preventing degradation of the organic light emitting device.

It should be noted that, the above display apparatus is not particularly limited to a switching device, and is easily applicable to a single crystal silicon substrate, an MIM device, an a-Si type, or the like in addition to the TFT device.

Hereinafter, the present invention is described specifically by way of examples. However, the present invention is not limited thereto.

EXAMPLE 1

Synthesis of Exemplified Compound P112

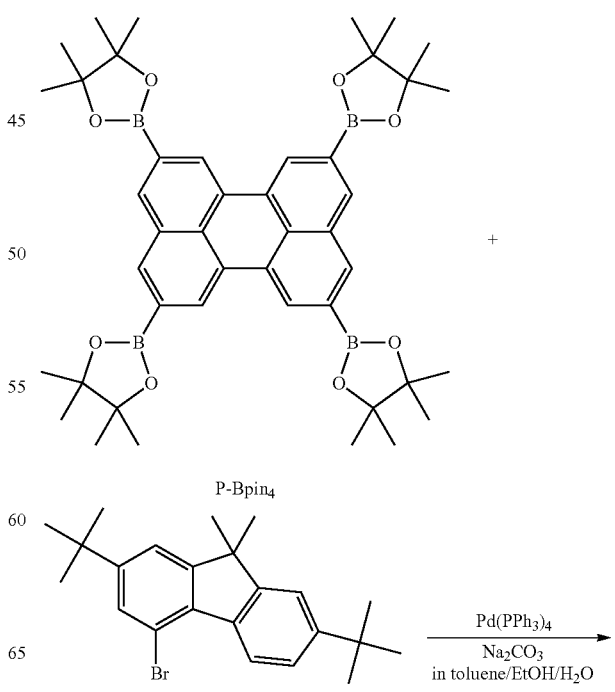

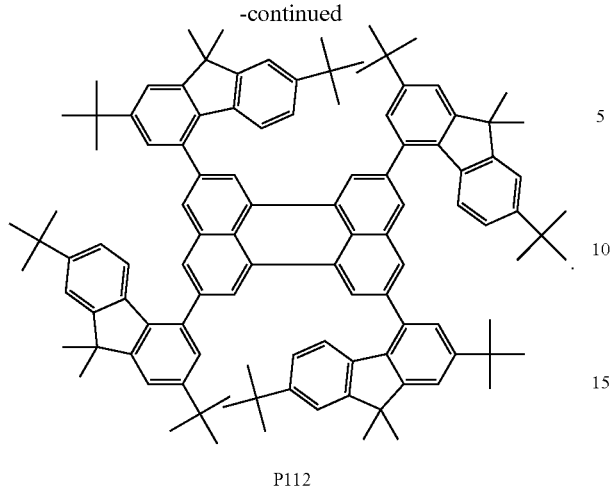

P112

Under a nitrogen atmosphere, the following reagents and solvents were charged into a 200-mL recovery flask.
Boronic acid ester P-Bpin$_4$: 1.0 g (1.32 mmol)
4-Bromo-2,7-di-tert-butyl-9,9-dimethylfluorene: 2.03 g (5.82 mmol)
Toluene: 60 mL
Ethanol: 30 mL Further, 30 mL of a 10 wt % sodium carbonate aqueous solution were added to the mixture, and after that, the reaction solution was stirred at room temperature for 30 minutes. Subsequently, 150 mg (0.13 mmol) of tetrakis(triphenylphosphine)palladium were added thereto, and then the reaction solution was stirred for 3 hours while being refluxed. After the completion of the reaction, the reaction solution was washed with water, dried over magnesium sulfate, and then concentrated. Next, the crude product was purified by reprecipitation with methanol, to give 0.59 g of Exemplified Compound P112 (yield: 30%).

The results of identification of the obtained compound are shown below.

[MALDI-TOF-MS: (Matrix Assisted Laser Desorption/Ionization Time-Of-Flight Mass Spectrometry)] Observed value: m/z=1,470.39, Calculated value: C$_{112}$H$_{124}$=1,468.97 [$^1$H-NMR (400 MHz, CDCl$_3$)] δ 8.40 (s, 4H), 7.84 (s, 4H), 7.55-7.27 (m, 12H), 7.23-6.85 (m, 8H), 1.52 (s, 24H), 1.38 (s, 36H), 1.29 (s, 36H)

EXAMPLE 2

Synthesis of Exemplified Compound P201

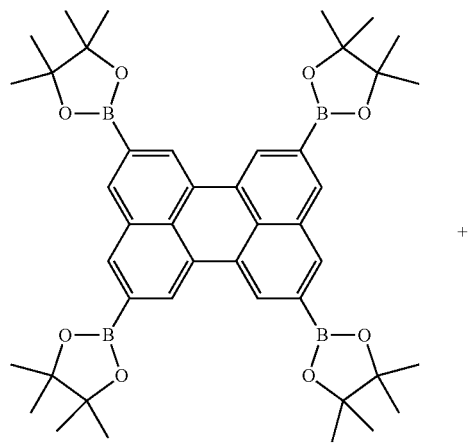

P-Bpin$_4$

+

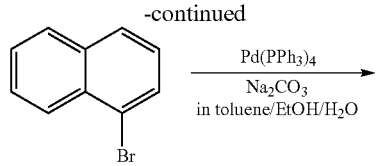

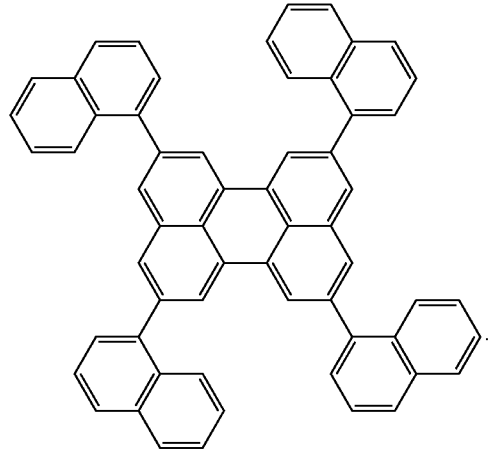

P201

Under a nitrogen atmosphere, the following reagents and solvents were charged into a 200-mL recovery flask.
Boronic acid ester P-Bpin$_4$: 1.0 g (1.32 mmol)
1-Bromonaphthalene: 1.20 g (5.82 mmol)
Toluene: 60 mL
Ethanol: 30 mL Further, 30 mL of a 10 wt % sodium carbonate aqueous solution were added to the mixture, and after that, the reaction solution was stirred at room temperature for 30 minutes. Subsequently, 150 mg (0.13 mmol) of tetrakis(triphenylphosphine)palladium were added thereto, and then the reaction solution was stirred for 3 hours while being refluxed. Next, the reaction solution was cooled and then a precipitated crystal was filtered, to thereby obtain a crude product. Next, the crude product was purified by recrystallization from toluene, to give 0.94 g of Exemplified Compound P201 (yield: 94%).

The results of the identification of the obtained compound are shown below.
<MALDI-TOF-MS> Observed value: m/z=756.11, Calculated value: C$_{60}$H$_{36}$=756.28 <$^1$H-NMR (400 MHz, CDCl$_3$)> δ 8.39 (s, 4H), 8.04 (d, 4H), 7.95-7.85 (m, 12H), 7.65-7.40 (m, 16H)

EXAMPLE 3

The organic light emitting device having the third layer structure described above was fabricated by a method shown below.

First, indium tin oxide (ITO) was formed into a film on a glass substrate (substrate) by a sputtering method so as to form an anode. At this time, the thickness of the anode was 120 nm. The thus obtained substrate on which ITO was formed into a film was used as a transparent conductive support substrate (ITO substrate). Next, the ITO substrate was transferred into a vacuum chamber of 10$^{-4}$ Pa, and after that, the following organic compound layer and electrode layer were each continuously formed as a film on the ITO substrate by vacuum deposition using resistance heating. Specifically, first, α-NPD was formed into a film on the anode, to thereby form a hole transport layer. At this time, the thickness of the hole transport layer was 15 nm. Next, on the hole transport layer, Compound BH-1 as a host and Exemplified Compound P201 as a guest were co-deposited, to thereby form an emission layer in such a manner that the content of Exemplified Compound P201 with respect to the entire emission layer became 2 wt %. At this time, the thickness of the emission layer was 30 nm. Next, Bphen was formed into a film on the emission layer, to thereby form an electron transport layer. At this time, the thickness of the electron transport layer was 20 nm. Next, KF was formed into a film on the electron transport layer, to thereby form a KF film. At this time, the thickness of the KF film was 1 nm. Next, Al was formed into a film on the KF film, to thereby form an Al film. At this time, the thickness of the Al film was 150 nm. Here, the KF film and the Al film function as a cathode.

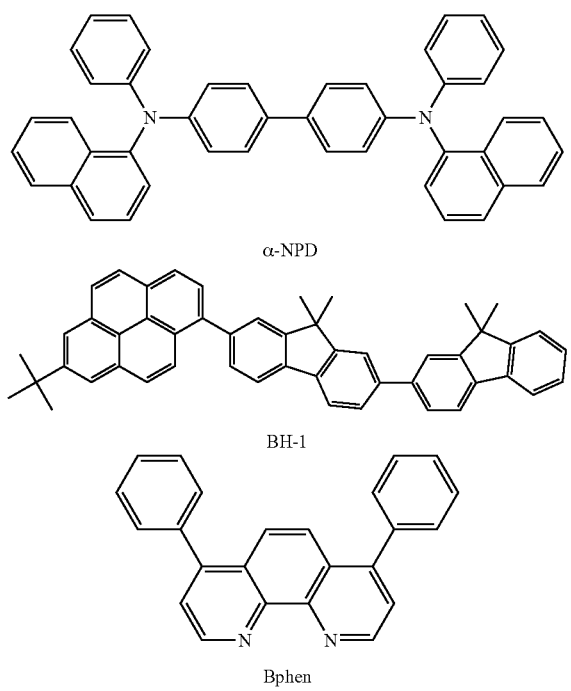

α-NPD

BH-1

Bphen

Next, the organic light emitting device was covered with a glass plate for protection in dry air atmosphere, and sealed with an acrylic resin-based adhesive so that the device might not be degraded by adsorption of moisture. The organic light emitting device was obtained as described above.

In the thus obtained organic light emitting device, a voltage of 4.5 V was applied to the device while the ITO electrode (anode) was used as a positive electrode and the Al electrode (cathode) was used as a negative electrode. As a result, the device was observed to emit blue light with a light emitting efficiency of 5.7 cd/A and a luminance of 2,000 cd/m$^2$. Further, the device had CIE chromaticity coordinates of (x, y)=(0.13, 0.26). In addition, when the device was subjected to durability drive for 100 hours while maintaining a constant current density of 100 mA/cm$^2$, a reduction rate in the luminance from the initial luminance was 20%.

COMPARATIVE EXAMPLE 1

A device was fabricated in the same manner as in Example 3 except that TBP shown below was used instead of Exemplified Compound P201 as a guest of an emission layer.

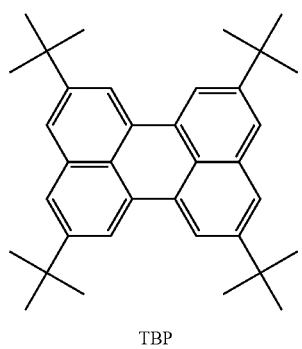

TBP

The obtained device was evaluated in the same manner as in Example 3. As a result, under an applied voltage of 5.1 V, the device was observed to emit blue-green light with a light emitting efficiency of 3.9 cd/A and a luminance of 2,000 cd/m$^2$. Further, the device had CIE chromaticity coordinates of (x, y)=(0.18, 0.35). In addition, when the device was subjected to durability drive for 100 hours while maintaining a constant current density of 100 mA/cm$^2$, a reduction rate in the luminance from the initial luminance was 48%.

EXAMPLE 4

The organic light emitting device having the third layer structure described above was fabricated.

First, an ITO substrate was fabricated by the same method as that of Example 3. Next, PEDOT (for organic EL) manufactured by Bayer A. G. was dropped onto the ITO substrate and the ITO substrate was spin-coated at 1,000 rpm for 30 seconds to form a thin film thereon. Next, the resultant was dried by heating inside a vacuum chamber at 120° C. for 1 hour, to thereby form a hole transport layer. At this time, the thickness of the hole transport layer was 35 nm. Next, the following reagent and solvent were mixed and an application liquid was prepared.

Dehydrated chloroform: 5.0 g
Exemplified Compound P112: 5 mg
Compound BH1: 50 mg Next, inside a glove box having a nitrogen atmosphere, the application liquid prepared above was dripped onto the hole transport layer and the hole transport layer was spin-coated at 2,000 rpm for 20 seconds. Next, the resultant was dried by heating inside a vacuum chamber at 120° C. for 1 hour, to thereby form an emission layer. At this time, the thickness of the emission layer was 45 nm.

Next, the ITO substrate in which layers up to the emission layer were formed was mounted inside a vacuum deposition chamber. Next, Bphen was vacuum-deposited on the emission layer, to thereby form an electron transport layer. At this time, the thickness of the electron transport layer was 40 nm. The organic compound layer formed on the ITO substrate, which was obtained from the above processes, has a total thickness of 120 nm. Next, KF was vacuum-deposited to form a KF film. At this time, the thickness of the KF film was 1 nm. Next, Al was vacuum-deposited on the KF film, to thereby form an Al film. At this time, the thickness of the Al film was 120 nm. Here, the KF film and the Al film function as a cathode. Thus, the organic light emitting device was obtained.

The characteristics of the obtained organic light emitting device was evaluated by using the ITO electrode (anode) as a positive electrode and the Al electrode (cathode) as a negative electrode and by applying a DC voltage to the device. The device had a current efficiency of 2.1 cd/A at a luminance of 500 cd/m². Further, an emission color at this time had CIE chromaticity coordinates of (x, y)=(0.14, 0.30).

EXAMPLE 5

The organic light emitting device having the third layer structure described above was fabricated by the following method.

An ITO substrate was fabricated by the same method as that of Example 3. Next, the ITO substrate was transferred into a vacuum chamber of $10^{-4}$ Pa, and after that, the following organic compound layer and electrode layer were each continuously formed as a film on the ITO substrate by vacuum deposition using resistance heating. Specifically, first, α-NPD was formed into a film on the anode, to thereby form a hole transport layer. At this time, the thickness of the hole transport layer was 20 nm. Next, on the hole transport layer, Exemplified Compound P201 as a host and GD-1 shown below as a guest were co-deposited from the vapor, to thereby form an emission layer in such a manner that the content of GD-1 with respect to the entire emission layer became 3 wt %. At this time, the thickness of the emission layer was 30 nm. Next, Bphen was formed into a film on the emission layer, to thereby form an electron transport layer. At this time, the thickness of the electron transport layer was 30 nm. Next, KF was formed into a film on the electron transport layer, to thereby form a KF film. At this time, the thickness of the KF film was 1 nm. Next, Al was formed into a film on the KF film, to thereby form an Al film. At this time, the thickness of the Al film was 120 nm. Here, the KF film and the Al film function as a cathode.

GD-1

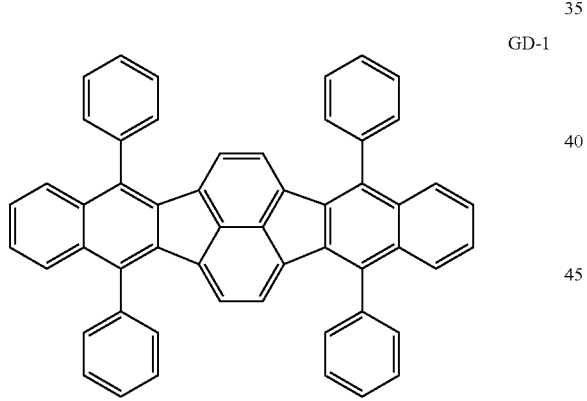

Next, the organic light emitting device was covered with a glass plate for protection in dry air atmosphere, and sealed with an acrylic resin-based adhesive so that the device might not be degraded by adsorption of moisture. The organic light emitting device was obtained as described above.

In the organic light emitting device, a voltage of 4.1 V was applied to the device while the ITO electrode (anode) was used as a positive electrode and the Al electrode (cathode) was used as a negative electrode. As a result, the device was observed to emit green light with a light emitting efficiency of 14.8 cd/A and a luminance of 1,800 cd/m². Further, the device had CIE chromaticity coordinates of (x, y)=(0.20, 0.69). In addition, when the device was subjected to durability drive for 200 hours while maintaining a constant current density of 100 mA/cm², a reduction rate in the luminance from the initial luminance was 26%.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-305859, filed on Dec. 1, 2008, which is hereby incorporated by reference herein in its entirety.

The invention claimed is:

1. An organic light emitting device, comprising:

an anode;

a cathode; and an organic compound layer which is sandwiched between the anode and the cathode, wherein one of the anode and the cathode is transparent or semi-transparent, wherein the organic compound layer is an emission layer comprising a host and a guest, wherein the guest comprises a perylene compound represented by the following general formula (1):

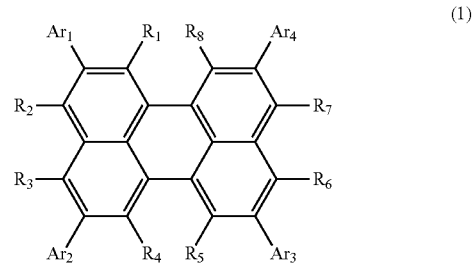

where $R_1$ to $R_8$ each represent a hydrogen atom or a substituted or unsubstituted alkyl group; and $Ar_1$ to $Ar_4$ each represent a substituent represented by the following general formula (2) or (3):

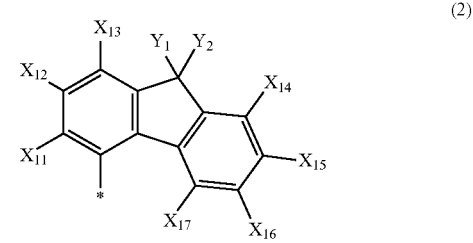

where $X_{11}$ to $X_{17}$ each represent a substituent selected from the group consisting of a hydrogen atom, a substituted or unsubstituted alkyl group, a substituted or unsubstituted aromatic hydrocarbon group, and a substituted or unsubstituted heterocyclic group, and adjacent substituents may be bonded to each other to form a ring structure; and $Y_1$ and $Y_2$ each represent a hydrogen atom or a substituted or unsubstituted alkyl group,

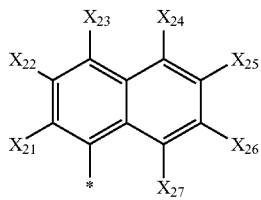

(3)

where $X_{21}$ to $X_{27}$ each represent a substituent selected from the group consisting of a hydrogen atom, a substituted or unsubstituted alkyl group, a substituted or unsubstituted aromatic hydrocarbon group, and a substituted or unsubstituted heterocyclic group, and adjacent substituents may be bonded to each other to form a ring structure, and wherein the light emission layer emits blue or green light.

2. The organic light emitting device according to claim 1, wherein the perylene compound is incorporated in the emission layer.

3. The organic light emitting device according to claim 1, comprising an electric field light emitting device which emits light by applying a voltage between the anode and the cathode.

4. A display apparatus comprising:
the organic light emitting device according to claim 1; and
a TFT device,
wherein one of the anode and the cathode of the organic light emitting device is connected to one of a source electrode and a drain electrode of the TFT device.

5. The organic light emitting device according to claim 1, wherein $Ar_1$ to $Ar_4$ all represent a fluorenyl group represented by the following general formula (4):

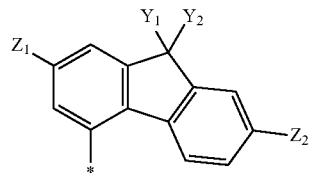

(4)

where $Y_1$, $Y_2$, $Z_1$, and $Z_2$ each represent a hydrogen atom or a substituted or unsubstituted alkyl group.

6. The organic light emitting device according to claim 1, wherein $Ar_1$ to $Ar_4$ all represent a naphthyl group represented by the following general formula (5):

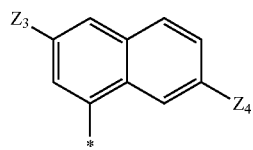

(5)

where $Z_3$ and $Z_4$ each represent a hydrogen atom or a substituted or unsubstituted alkyl group.

* * * * *